US012667349B2

(12) United States Patent
Sugimoto et al.

(10) Patent No.: US 12,667,349 B2
(45) Date of Patent: Jun. 30, 2026

(54) FULL-THICKNESS RESECTION METHOD

(71) Applicants: OLYMPUS CORPORATION, Hachioji (JP); NATIONAL CANCER CENTER, Tokyo (JP)

(72) Inventors: Arimasa Sugimoto, Hachioji (JP); Satoru Nonaka, Tokyo (JP)

(73) Assignees: OLYMPUS CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 838 days.

(21) Appl. No.: 17/941,545

(22) Filed: Sep. 9, 2022

(65) Prior Publication Data

US 2024/0081796 A1    Mar. 14, 2024

(51) Int. Cl.
*A61B 17/00*      (2006.01)
*A61B 17/04*      (2006.01)

(52) U.S. Cl.
CPC .... *A61B 17/00234* (2013.01); *A61B 17/0469* (2013.01); *A61B 2017/00296* (2013.01)

(58) Field of Classification Search
CPC .......... A61B 17/00234; A61B 17/0469; A61B 2017/00296; A61B 2017/00349; A61B 2018/00982; A61B 2018/1412; A61B 17/072; A61B 2017/00818; A61B 2017/07278; A61B 2017/00269; A61B 2017/00278; A61B 2018/00494; A61B 2017/111; A61B 17/1114; A61F 5/0083; A61F 5/0086
See application file for complete search history.

(56) References Cited

U.S. PATENT DOCUMENTS

| 2010/0030019 A1* | 2/2010 | Kuroda | .............. A61B 17/0401 600/106 |
| 2018/0160916 A1* | 6/2018 | Madsen | ............... A61B 5/4552 |
| 2019/0357934 A1* | 11/2019 | Borek | ............ A61B 17/320016 |

FOREIGN PATENT DOCUMENTS

JP          2010-036024 A      2/2010

* cited by examiner

*Primary Examiner* — Brooke Labranche
*Assistant Examiner* — Rachael L Geiger
(74) *Attorney, Agent, or Firm* — Oliff PLC

(57) ABSTRACT

A full-thickness resection method for a gastrointestinal tract includes forming a pair of first markings in surrounding tissue on both sides of a lesion to sandwich the lesion therebetween; performing a full-thickness resection to a portion including the lesion; identifying a pair of suture locations in the vicinity of the pair of first markings; and suturing the pair of first suture locations.

12 Claims, 16 Drawing Sheets

FULL-THICKNESS RESECTION METHOD

TECHNICAL FIELD

The present disclosure relates to a full-thickness resection method for perfuming the full-thickness resection with respect to the gastrointestinal tract and the like.

BACKGROUND

In recent years, the endoscopic full-thickness resection (EFTR) has been used in the surgery of full-thickness resection with respect to the gastrointestinal tract and the like. When the gastrointestinal tract such as the stomach is full-thickness resected, the air in the gastrointestinal tract escapes to the abdominal cavity side and the shape of the gastrointestinal tract changes such that it is difficult for the surgeon to grasp the site to be sutured.

In Japanese Unexamined Patent Application, First Publication No. 2010-036024, a suturing device that is attached to an endoscope and used is described. The surgeon can use the endoscope attached with a suturing device to perform procedures of resecting and suturing a portion of the gastrointestinal tract including a lesion. Before performing the full-thickness resection of the portion including the lesion, the surgeon marks the periphery of the lesion to clarify the position of the lesion.

SUMMARY

A full-thickness resection method according to a first aspect of the present disclosure is a method of full-thickness resection of a gastrointestinal tract including forming a pair of first markings in peripheral tissues on both sides of a lesion to sandwich the lesion, performing a full-thickness resection of a portion including the lesion, specifying a vicinity of the pair of the first markings as a pair of first suture locations, and suturing the pair of first suture locations.

DETAILED DESCRIPTION

First Embodiment

A first embodiment of the present disclosure will be described with reference to FIG. 1 to FIG. 15.

Figure 1:
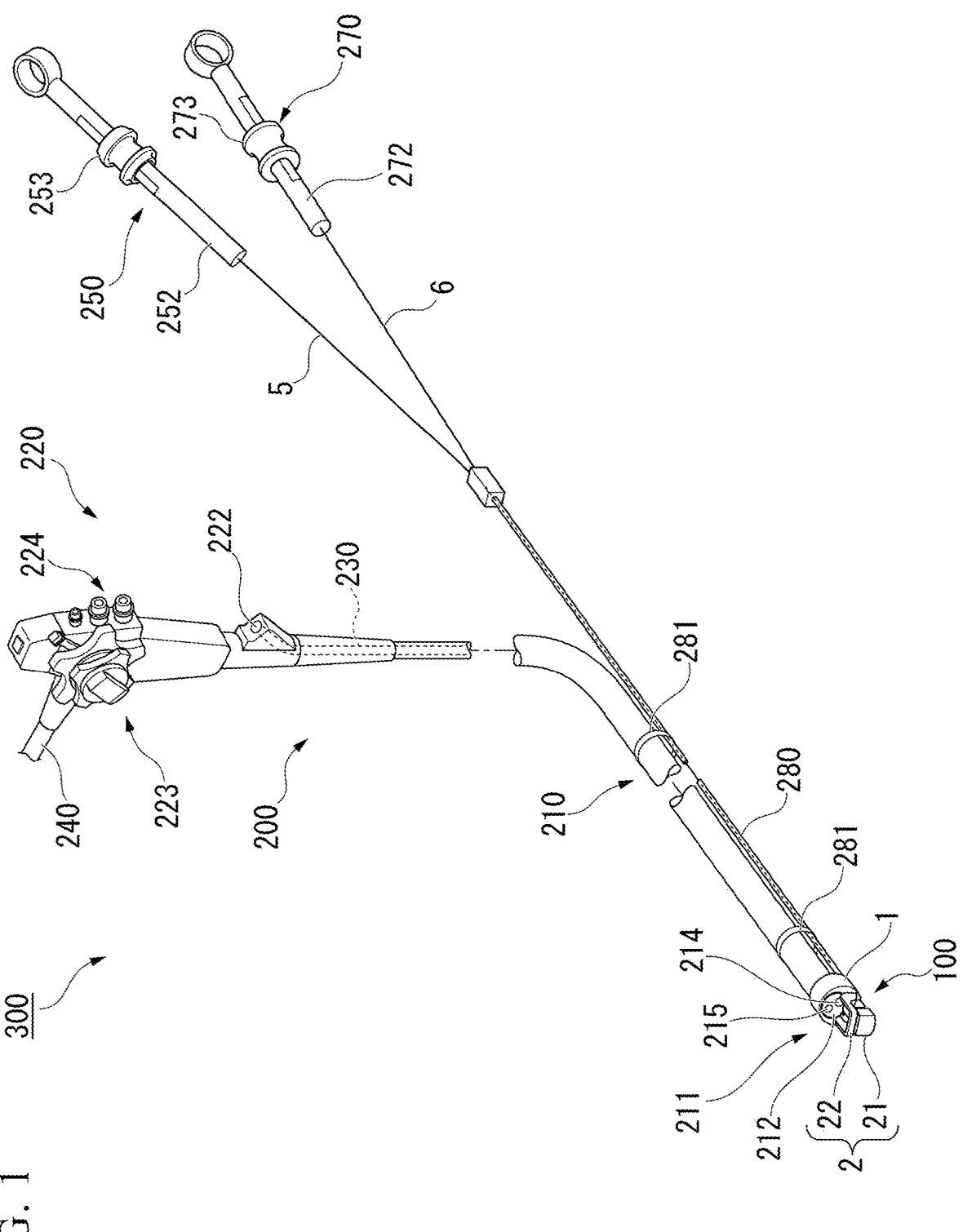
FIG. 1 is a view showing a medical system used for the full-thickness resection method according to a first embodiment of the present disclosure.

FIG. 1 is a view showing an overall configuration of a medical system 300 used in a full-thickness resection method according to the present embodiment. It is noted that the medical system used for the full-thickness resection method according to the present embodiment is not limited to the medical system 300.

[Medical System 300]

The medical system 300 is used for operations such as suturing the gastrointestinal tract. The medical system 300 includes a medical stapler 100, an endoscope 200, an open-close operation portion 250, an ejection operation portion 270 and a wire sheath 280. The open-close operation portion 250 is an operation portion that operates the medical stapler 100 with the open-close operation wire 5. The ejection operation portion 270 is an operation portion that operates the medical stapler 100 with an ejection operation wire 6.

[Endoscope 200]

The endoscope 200 is a conventional flexible endoscope, and includes an elongated insertion portion 210 inserted into the body from a distal end, an operation portion 220 provided at a proximal end portion of the insertion portion 210, and a universal cord 240, provided.

A treatment device channel 230 for inserting through an endoscopic treatment device is formed in the insertion portion 210. A distal end 212 of the insertion portion 210 is provided with a forceps port 214 that is a distal opening of the treatment device channel 230. The treatment device channel 230 extends from the distal end 212 of the insertion portion 210 to the operation portion 220.

A distal end portion 211 of the insertion portion 210 includes an imaging unit (not shown) having a CCD or the like. An objective lens 215 of the imaging unit is exposed at the distal end 212 of the insertion portion 210.

A knob 223 for operating the insertion portion 210 and a switch 224 for operating the imaging unit and the like are provided on the proximal end side of the operation portion 220. The surgeon can bend the insertion portion 210 in a desired direction by operating the knob 223.

A forceps insertion port 222 that communicates with the treatment device channel 230 is provided on the distal end side of the operation portion 220. The surgeon can insert the endoscopic treatment device into the treatment device channel 230 through the forceps insertion port 222.

A universal cord 240 connects the operation portion 220 and an external peripheral device. The universal code 240 outputs, for example, an image captured by the imaging unit to an external device. An image captured by the imaging unit is displayed on a display device such as a liquid crystal display via an image processing device.

[Open-Close Operation Portion 250]

The open-close operation portion 250 is an operation part that opens and closes the medical stapler 100 by operating the open-close operation wire 5. The open-close operation portion 250 has an open-close operation portion main body 252 and an open-close operation slider 253 as shown in FIG. 1. A proximal end of the open-close operation wire 5 is connected to the open-close operation slider 253.

The surgeon can advance and retract the open-close operation wire 5 by advancing and retracting the open-close operation slider 253 with respect to the open-close operation portion main body 252 in the longitudinal axis direction.

[Ejection Operation Unit 270]

The ejection operation unit 270 is an operation unit that ejects (injects) the staples S from the medical stapler 100 by operating the ejection operation wire 6. The ejection operation portion 270 has an ejection operation portion main body 272 and an ejection operation slider 273, as shown in FIG. 1. A proximal end of the ejection operation wire 6 is connected to the ejection operation slider 273. The surgeon can advance and retract the ejection operation wire 6 by advancing and retracting the ejection operation slider 273 with respect to the ejection operation portion main body 272 in the longitudinal direction.

[Wire Sheath 280]

The wire sheath 280 is a sheath through which the open-close operation wire 5 and the ejection operation wire 6 are inserted. As shown in FIG. 1, the distal end side of the wire sheath 280 is connected to the insertion portion 210 of the endoscope 200 by a band 281.

[Medical Stapler 100]

Figure 2:
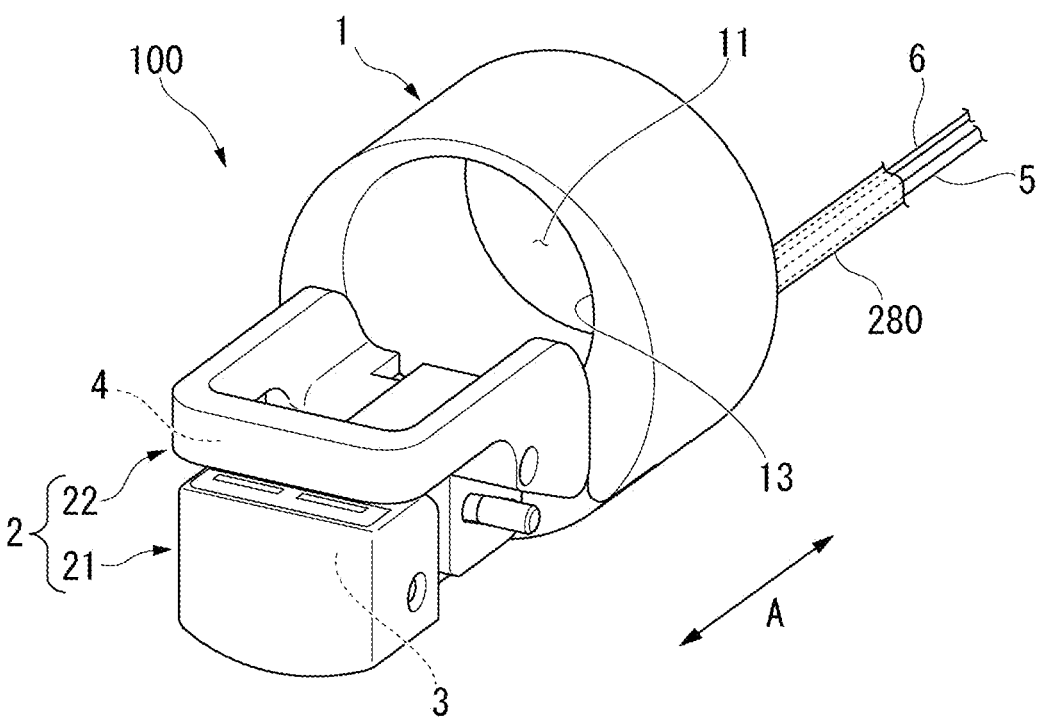
FIG. 2 is a perspective view showing the medical stapler.

FIG. 2 is a perspective view of the medical stapler 100.

The medical stapler (suture device) 100 includes a cap 1, a grasping portion 2, a staple ejection portion 3, a staple receiving portion 4, the open-close operation wire 5, and the ejection operation wire (power transmission member) 6. The medical stapler 100 is attachable to and detachable from the distal end portion 211 of the insertion portion 210.

Figure 3:
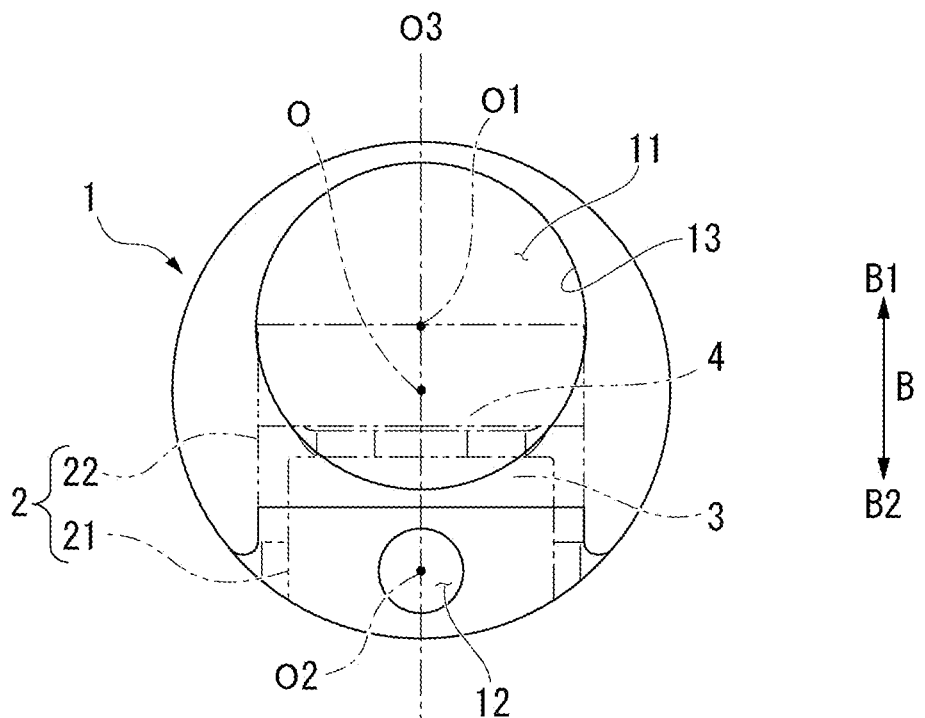
FIG. 3 is a front view showing a cap of the medical stapler.

FIG. 3 is a front view of the cap 1. In FIG. 3, the grasping portion 2 is displayed transparently.

The cap (detachable portion) 1 is a member attachable to and detachable from the distal end portion 211 of the endoscope 200. The cap 1 is formed in a substantially cylindrical shape and has a first through hole 11 penetrating in the axial direction A and a second through hole 12 penetrating in the axial direction A.

The first through hole 11 is a hole into which the distal end portion 211 of the insertion portion 210 of the endoscope 200 is inserted. The shape of the first through hole 11 is formed to follow the outer shape of the distal end portion 211 of the insertion portion 210. Therefore, by inserting the distal end portion 211 of the endoscope 200 into the first through hole 11, the cap 1 can be attached to the distal end portion 211 of the endoscope 200.

A central axis O1 of the first through hole 11 in the axial direction A is eccentric with respect to the central axis O of the cap 1 in the axial direction A, as shown in FIG. 3. The direction in which the central axis O1 is eccentric with respect to the central axis O is defined as an "upper side B1".

The second through hole 12 is a hole into which the wire sheath 280 through which the open-close operation wire 5 and the ejection operation wire 6 are inserted is inserted. An inner diameter of the second through hole 12 substantially matches the outer diameter of the wire sheath 280. The distal-end portion of the wire sheath 280 is inserted through the second through hole 12 and fixed. The open-close operation wire 5 and the ejection operation wire 6 passing through the wire sheath 280 pass through the second through hole 12 and extend to the distal-end side.

The central axis O2 of the second through hole 12 in the axial direction A is eccentric with respect to the central axis O of the cap 1 in the axial direction A, as shown in FIG. 3. The direction in which central axis O2 is eccentric with respect to central axis O is opposite to the direction in which central axis O1 is eccentric with respect to central axis O (the upper side B1). The direction in which the central axis O2 is eccentric with respect to central axis O is defined as a "lower side B2". In the present embodiment, the upper side B1 and the lower side B2 are directions along the up-down direction B.

Figure 4:
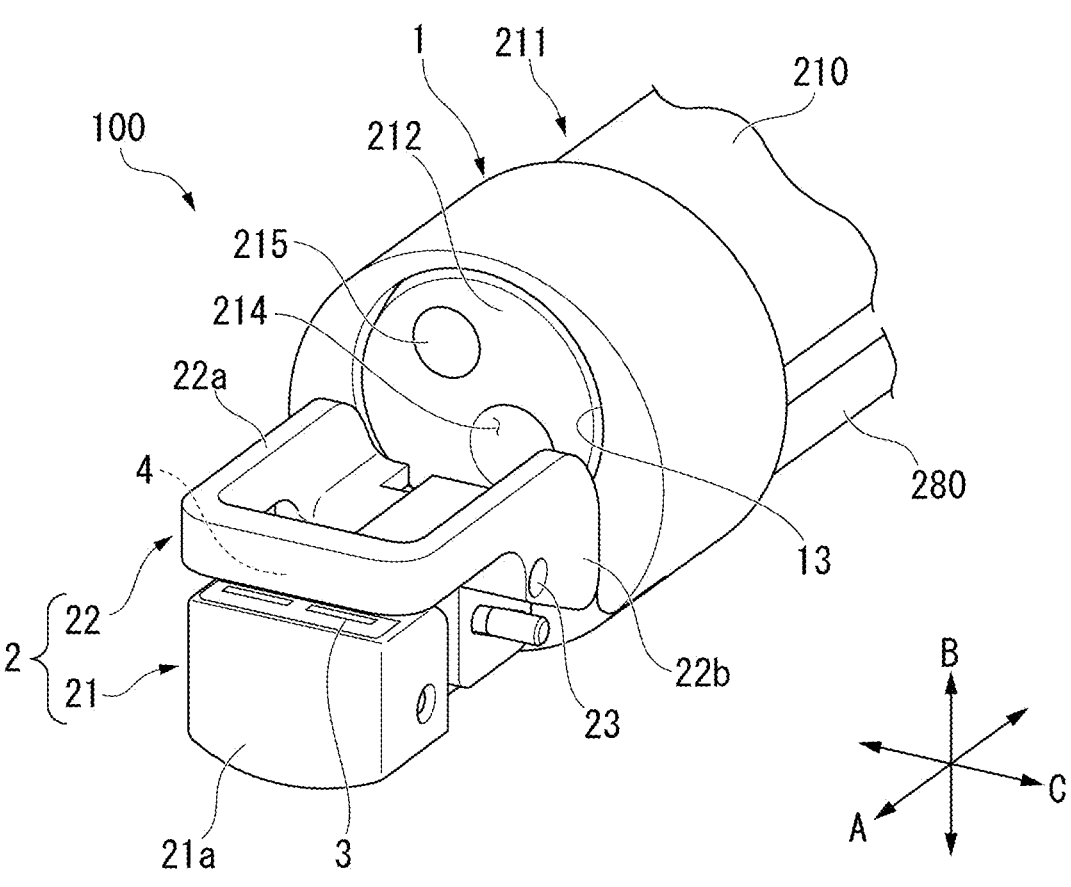
FIG. 4 is a perspective view showing the medical stapler in which a grasping portion is in a closed state.
Figure 5:
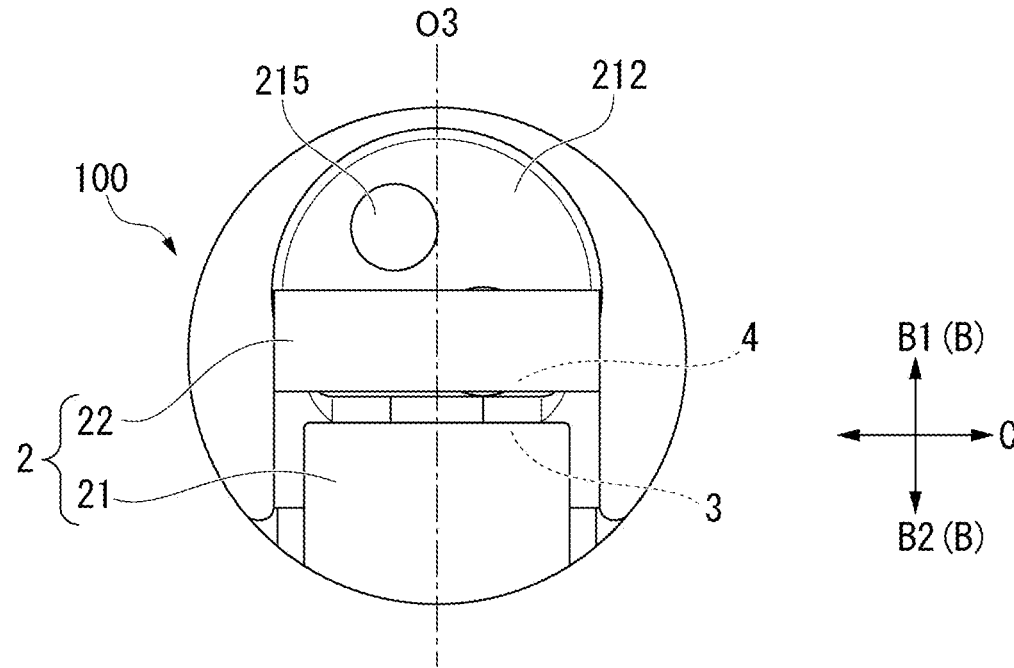
FIG. 5 is a front view showing the medical stapler in which the grasping portion is in the closed state.

FIG. 4 and FIG. 5 are a perspective view and a front view of the medical stapler 100 with the grasping portion 2 in a closed state, respectively.

When the cap 1 is attached to the distal end portion 211 of the endoscope 200, as shown in FIG. 4 and FIG. 5, the objective lens 215 and the forceps port 214 are exposed outside through the opening 13 on the distal-end side of the first through hole 11 of the cap 1. The surgeon can observe the treatment target through the objective lens 215 even when the medical stapler 100 is attached to the distal end portion 211 of the endoscope 200.

Figure 6:
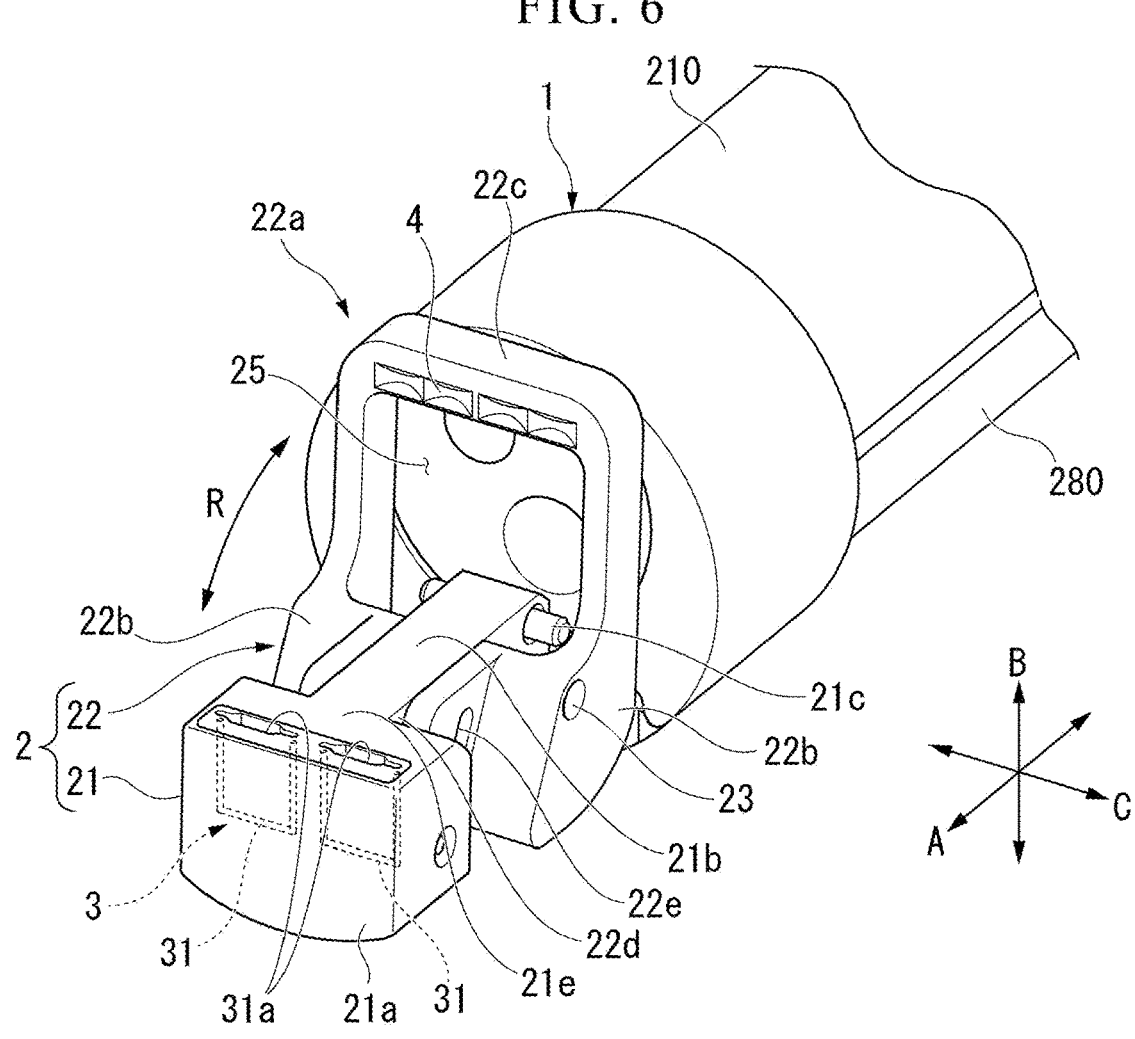
FIG. 6 is a perspective view showing the medical stapler in which the grasping portion is in an open state.
Figure 7:
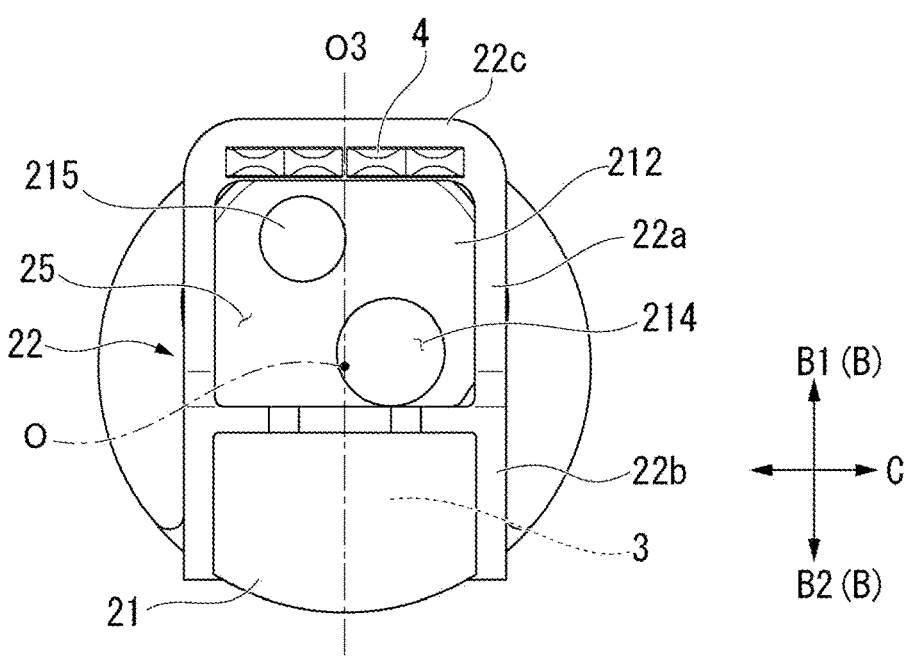
FIG. 7 is a front view showing the medical stapler in which the grasping portion is in the open state.
Figure 8:
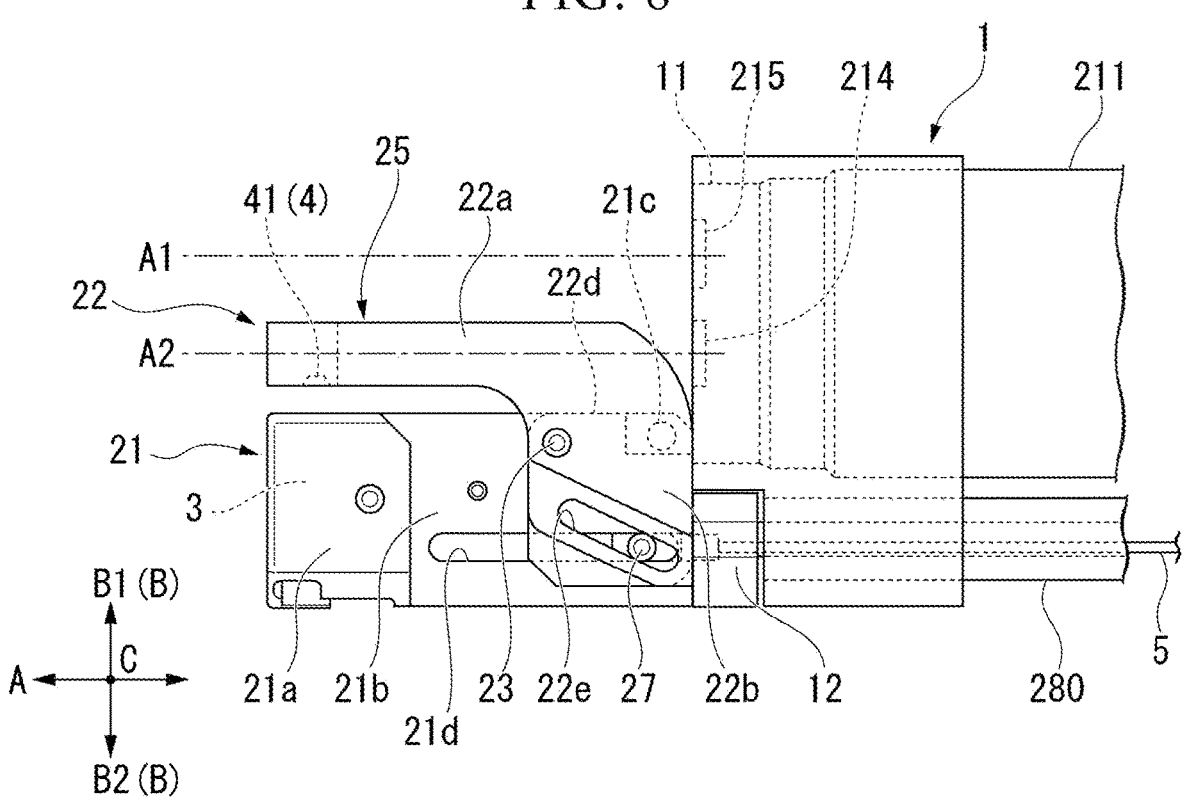
FIG. 8 is a side view showing the medical stapler in which the grasping portion is in the closed state.
Figure 9:
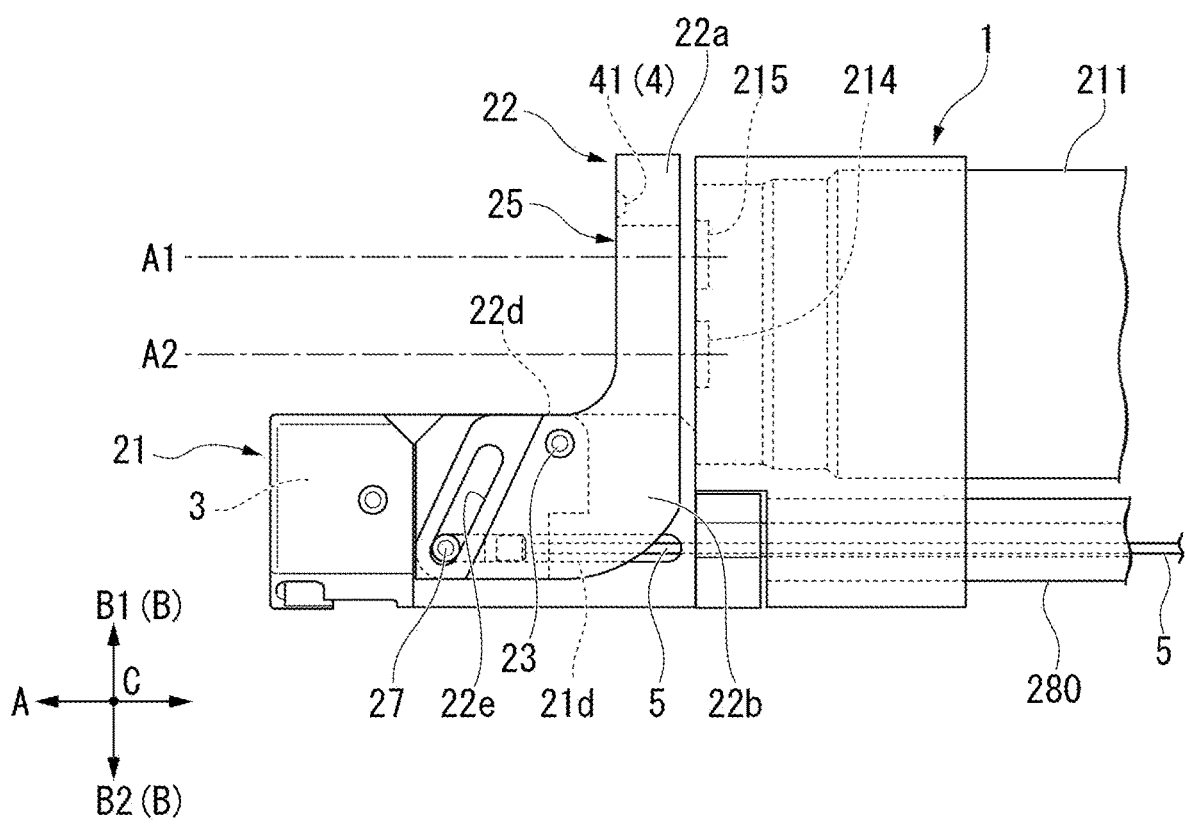
FIG. 9 is a side view showing the medical stapler in which the grasping portion is in the open state.

FIG. 6 and FIG. 7 are a perspective view and a front view of the medical stapler 100 with the grasping portion 2 in an open state, respectively. Furthermore, FIG. 8 is a side view of the medical stapler 100 with the grasping portion 2 in the closed state. FIG. 9 is a side view of the medical stapler 100 with the grasping portion 2 in the open state.

As shown in FIG. 8, the grasping portion 2 has a first grasping member 21, a second grasping member 22, an open-close rotating shaft 23, and a movable pin 27. The first grasping member 21 and the second grasping member 22 are connected to each other by the open-close rotating shaft 23 so as to be openable and closable. The open-close rotating shaft 23 is provided on the distal-end side of the cap 1. The axial direction C of the open-close rotating shaft 23 is perpendicular to the axial direction A and the up-down direction B of the cap 1. The grasping portion 2 is formed symmetrically with respect to the central axis O3 in the up-down direction B, as shown in FIG. 7.

The first grasping member 21 is non-rotatably fixed to the distal-end side of the cap 1. The first grasping member 21 is fixed to the cap 1 at a position B2 below the central axis O of the cap 1. The first grasping member 21 is arranged at a position overlapping the second through hole 12 in the front view, as shown in FIG. 3. On the other hand, as shown in FIG. 7, the first grasping member 21 is arranged at a position not overlapping the objective lens 215 and the forceps port 214 of the endoscope 200 when viewed from the front.

As shown in FIG. 6, the first grasping member 21 has a first distal-end portion 21a and a first main body portion 21b, and is formed in a substantially T shape in a plan view. The first distal-end portion 21a is arranged at the distal-end side with respect to the first main body portion 21b.

The first distal-end portion 21a is formed in a substantially rectangular parallelepiped shape. The first distal-end portion 21a is formed in a rectangular shape extending in the axial direction C of the open-close rotating shaft 23 in the plan view. The staple ejection portion 3 is provided at the first distal-end portion 21a. An opening 31a of the staple ejection portion 3 is provided on a surface (upper surface 21e) at the upper side B1 of the first distal-end portion 21a.

The first main body portion 21b is an elongated member extending in the axial direction A. The distal end of the first main body portion 21b is fixed to the first distal-end portion 21a. A proximal end of the first main body portion 21b is fixed to the cap 1 via the wire sheath 280. The first main body portion 21b has a contact pin 21c and a first engagement groove 21d (FIG. 8).

The contact pin 21c is provided at the proximal end of the first main body portion 21b so as to contact the second grasping member 22 in the closed state for restricting a movable range of the second grasping member 22.

As shown in FIG. 8, the first engagement groove 21d is a groove penetrating in the axial direction C of the open-close rotating shaft 23 in the first main body portion 21b. The first engaging groove 21d extends in the axial direction A.

The second grasping member 22 is rotatably attached to the first grasping member 21 by the open-close rotating shaft 23. The second grasping member 22 has a U-shaped member 22a formed substantially in a U-shape and a second main body portion 22b that rotatably supports the U-shaped member 22a.

The U-shaped member 22a is formed in a substantially U-shape, both end portions of which are connected to the second main body portion 22b, and the central portion thereof is arranged on the distal-end side. As shown in FIG. 7, the central portion has a second distal-end portion 22c. The second distal-end portion 22c is formed in a substantially rectangular parallelepiped shape. The staple receiving portion 4 is provided at the second distal-end portion 22c.

The second main body portion 22b is rotatably attached to the first main body portion 21b of the first grasping member 21 by the open-close rotating shaft 23. A guide groove 22d into which the first main body portion 21b is inserted is formed in the second main body portion 22b. Second engagement grooves 22e are formed on both sides of the guide groove 22d of the second main body portion 22b.

The second engagement groove 22e is a groove formed in the second main body portion 22b. The second engagement groove 22e is a groove penetrating in the axial direction C. The second engagement groove 22e is formed on the side opposite to the staple receiving portion 4 with the open-close rotating shaft 23 interposed therebetween in a side view. The second engagement groove 22e is formed symmetrically with respect to the central axis O3 of the second grasping member 22.

As shown in FIG. 6, the second grasping member 22 has a visual field space 25 penetrating in the open-close direction R between the staple receiving portion 4 on the distal-end side and the open-close rotating shaft 23 on the proximal-end side. In the present embodiment, the visual field space 25 is a space surrounded by sides of the U-shaped member 22a formed in a substantially U-shape.

As shown in FIG. 8, the movable pin 27 engages with the first engagement groove 21d and the second engagement groove 22e, and advances and retracts in the axial direction A along the first engagement groove 21d. The distal end of the open-close operation wire 5 is attached to the movable pin 27. As the open-close operation wire 5 advances, the movable pin 27 rotates the second grasping member 22 about the open-close rotating shaft 23 as shown in FIG. 9, and the grasping portion 2 enters the open state. When the open-close operation wire 5 retracts toward the proximal-end side, the movable pin 27 rotates the second grasping member 22 about the open-close rotating shaft 23 as shown in FIG. 8, and the grasping portion 2 enters the closed state.

When the grasping portion 2 is in the closed state, the staple ejection portion 3 and the staple receiving portion 4 face each other as shown in FIG. 5. A slight gap is formed between the staple ejection portion 3 and the staple receiving portion 4 when the grasping portion 2 is in the closed state. When the grasping portion 2 is in the closed state, the optical axis A1 of the objective lens 215 passes through the upper side B1 of the first grasping member 21 and the second grasping member 22, as shown in FIG. 8. Further, when the grasping portion 2 is in the closed state, the central axis A2 of the forceps port 214 does not overlap the first grasping member 21 in the front view; however, the central axis A2 of the forceps port 214 is positioned to overlap the second grasping member 22.

When the grasping portion 2 is in the open state, the staple receiving portion 4 is arranged at the proximal-end side of the open-close rotating shaft 23, as shown in FIG. 9. When the grasping portion 2 is in the open state, the staple ejection portion 3 and the staple receiving portion 4 are arranged at the upper side B1 and the lower side B2 respectively with the optical axis A1 of the objective lens 215 interposed therebetween. The optical axis A1 of the objective lens 215 passes through the visual field space 25 when the grasping portion 2 is in the open state. Also, when the grasping portion 2 is in the open state, the central axis A2 of the forceps port 214 passes through the visual field space 25.

Figure 10:
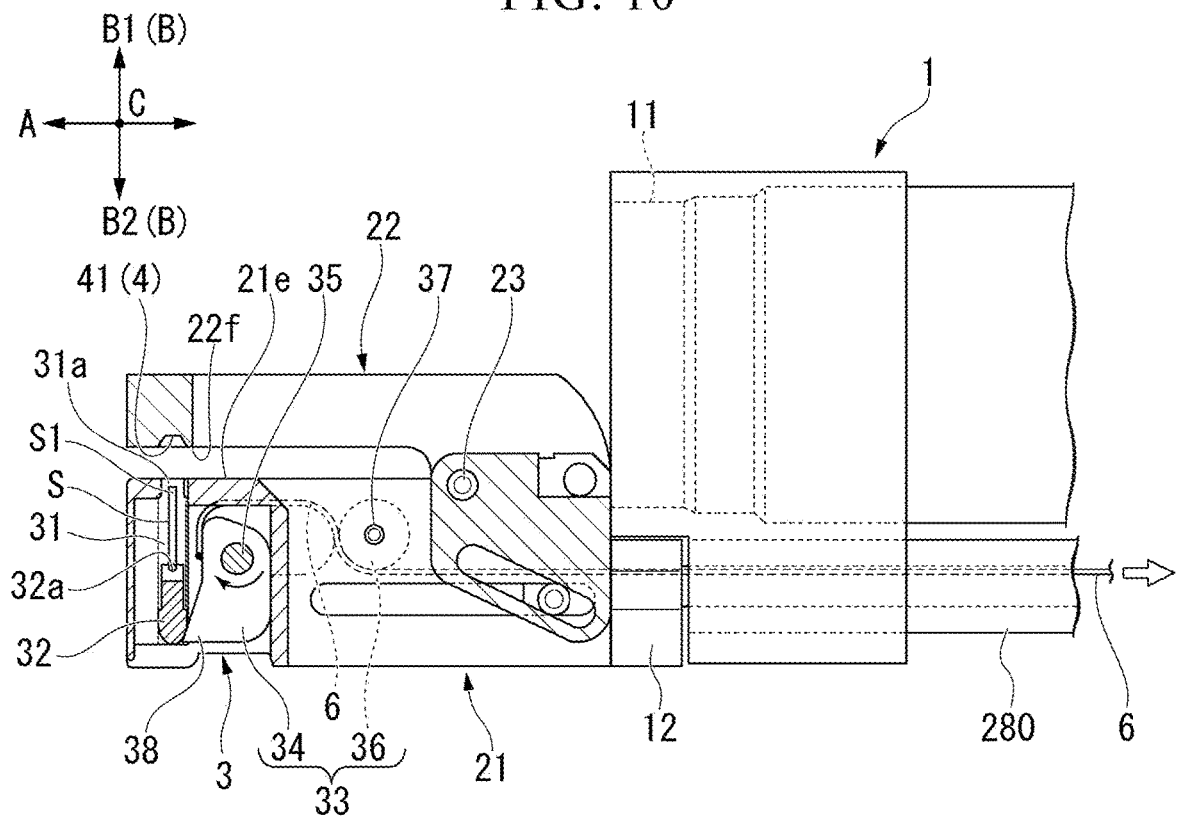
FIG. 10 is a cross-sectional view showing the grasping portion including a staple ejection portion.

FIG. 10 is a cross-sectional view of grasping portion 2 including the staple ejection portion 3.

The staple ejection portion 3 is provided at the first distal-end portion 21a of the first grasping member 21, and can store and eject the staples S. The staple ejection portion 3 has a staple storage portion 31, a rectilinear member 32 and a rotating member 33.

The staple storage portion 31 is a space for storing the staples S provided at the first distal-end portion 21a of the first grasping member 21. In the first grasping member 21, two staple storage portions 31 as shown in FIG. 6 are arranged side by side in the axial direction C so as to be able to store two U-shaped staples S therein.

The staple storage portion 31 opens in the up-down direction B at an opening 31a provided on the upper surface 21e of the first distal-end portion 21a. The staple S is stored in the staple storage portion 31 through the opening 31a. The staple S is stored in the staple storage portion 31 with the needle tip S1 of the staple S directed toward the upper side B1.

The staple storage portion 31 is formed in a rectangular shape with a short side extending in the axial direction A and a long side extending in the axial direction C in the plan view. The needle tips S1 at both ends of the staples S stored in the staple storage portion 31 are arrayed in the axial direction C.

The rectilinear member 32 is a member accommodated in the staple storage portion 31 and is movable in the up-down direction B in the internal space of the staple storage portion 31. The rectilinear member 32 has a concave portion 32*a* for supporting the staple S in the upper side B1. The staples S stored in the staple storage portion 31 are able to be fitted into the concave portion 32*a*.

A first pulley 34 and a second pulley 36 as the rotating member 33 are rotatably attached to the inside of the first grasping member 21, and move the rectilinear member 32 in the up-down direction B by rotating. A first rotation shaft 35 of the first pulley 34 and a second rotation shaft 37 of the second pulley 36 extend in the axial direction C and are substantially parallel to the open-close rotating shaft 23 of the gripper 2.

The first pulley 34 is rotatable around the first rotating shaft 35 as a center. The distal end of the ejection operation wire 6 is connected to the first pulley 34, and the first pulley 34 rotates when the ejection operation wire 6 is pulled. The first pulley 34 has a convex portion (abutting portion) 38 that supports the rectilinear member 32 from the lower side B2 on the distal end side.

The second pulley 36 is rotatable around the second rotating shaft 37 as a center. The second pulley 36 is arranged at the proximal-end side than the first pulley 34 and is a bending pulley that changes the advancing direction of the ejection operation wire 6.

The distal end of the ejection operation wire 6 is connected to the first pulley 34 at the upper side B1 of the first rotating shaft 35. The ejection operation wire 6 extends from the first pulley 34 to the ejection operation portion 270 via the second pulley 36 and passing through the second through hole 12.

Figure 11:
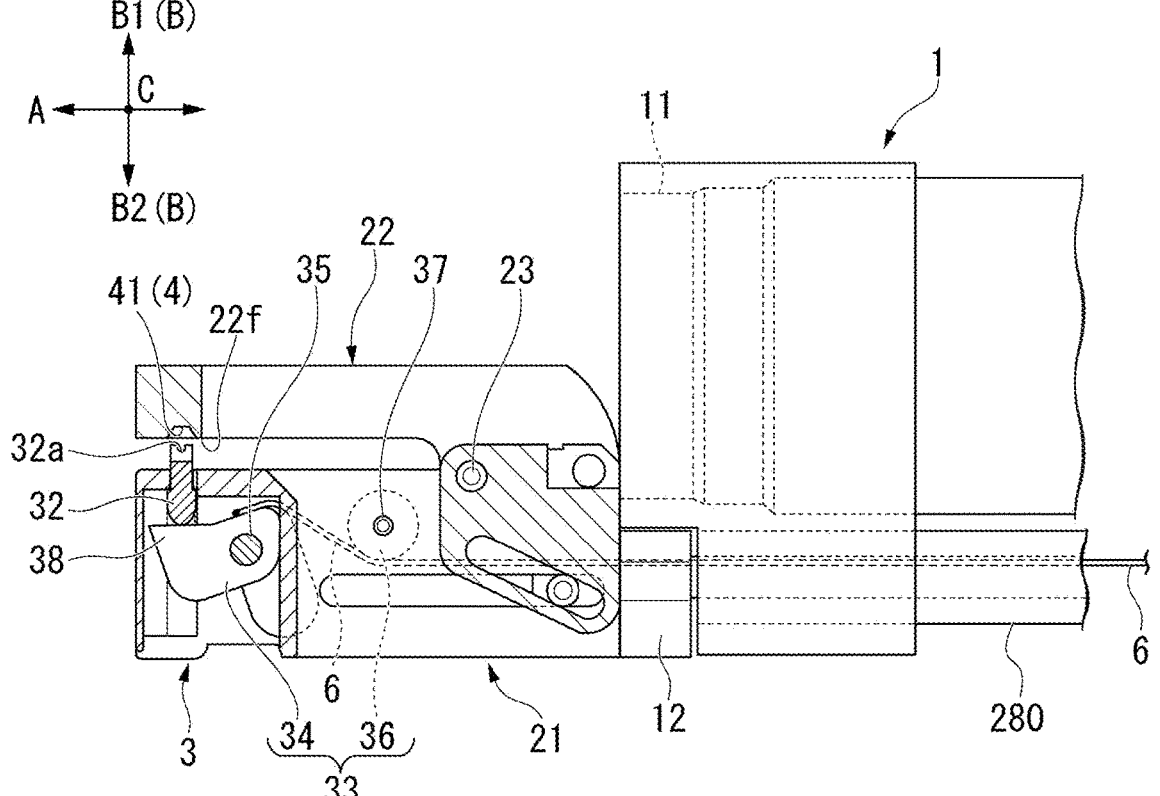
FIG. 11 is a cross-sectional view showing the grasping portion in which an ejection operation wire is pulled.

FIG. 11 is a cross-sectional view of the grasping portion 2 with the ejection operation wire 6 being pulled.

As the ejection operation wire 6 is pulled, the first pulley 34 rotates, and the convex portion 38 of the first pulley 34 pushes the rectilinear member 32 to the upper side B1, and the stored staple S are ejected toward the upper side B1 from the opening 31*a*.

The staple receiving portion (anvil) 4 is provided on the lower surface 22*f* of the second distal-end portion 22*c* of the second grasping member 22. The staple receiving portion 4 is provided with a plurality of pockets 41 capable of receiving the staples S ejected from the staple ejecting portion 3. In the present embodiment, since two U-shaped staples are ejected from the staple ejection portion 3, the staple receiving portion 4 is provided with four pockets. When the grasping portion 2 is in the closed state, the opening 31*a* through which the staple S is ejected and the pocket 41 of the staple ejection portion 3 face each other.

[Method of Using Medical Stapler 100]

Next, a method of using the medical stapler 100 (a method of full-thickness resection using the medical stapler 100) will be described. Specifically, a method for full-thickness resection of a lesion TU formed in the stomach by the endoscopic treatment will be described.

<Insertion Step>

A surgeon or an assistant (hereinafter simply referred to as a "surgeon") inserts the insertion portion 210 of the endoscope 200 without the medical stapler 100 being attached thereto through the mouth, which is a natural orifice, and approaches the distal end portion 211 to the treatment target T. The surgeon operates the open-close operation portion 250 to make the open-close operation wire 5 to advance so as to put the grasping portion 2 into the open state. It is noted that the surgeon may attach the medical stapler 100 to the endoscope 200 from the insertion step.

<Line Identification Step>

Figure 12:
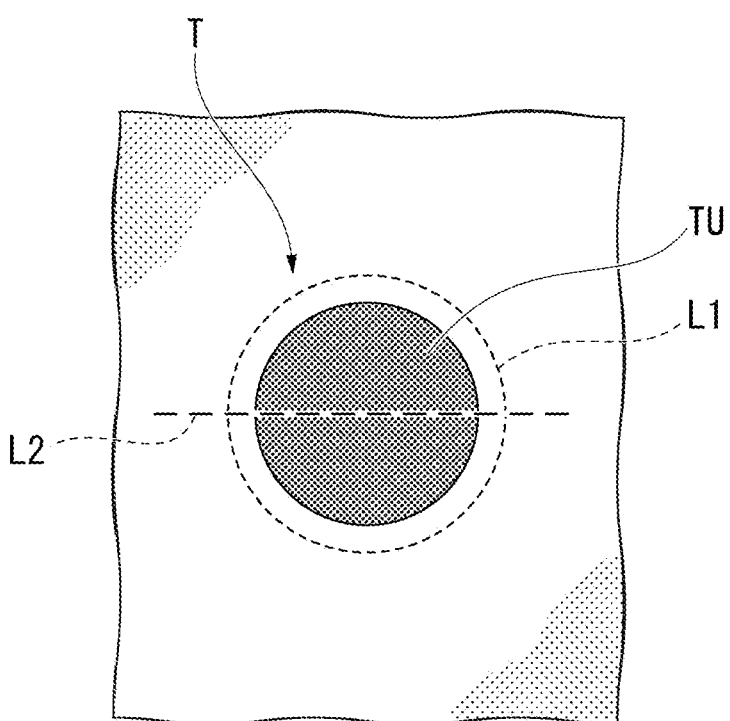
FIG. 12 is a view showing an incision line and a suture line that are certified.

FIG. 12 is a view showing an identified incision line L1 and a suture line L2.

Based on the position and shape of the lesion TU, the surgeon identifies an incision line L1 around the lesion TU for the full-thickness resection. The surgeon performs a circumferential incision of the mucosal layer MU1 along the incision line L1. Before performing the circumferential incision, the surgeon may perform marking (hereinafter also referred to as "specific marking") used to identify the lesion TU. The specific marking is formed, for example, along the incision line L1.

The surgeon identifies the suture line L2 from the shape of the incision line L1. The suture line L2 is a line along which the defect D after the full-thickness resection is sutured. It is desirable that the suture line L2 is identified such that the grasping portion 2 of the medical stapler 100 can easily grasp a pair of sutured portions facing each other with the suture line L2 interposed therebetween.

<Marking Step>

Figure 13:
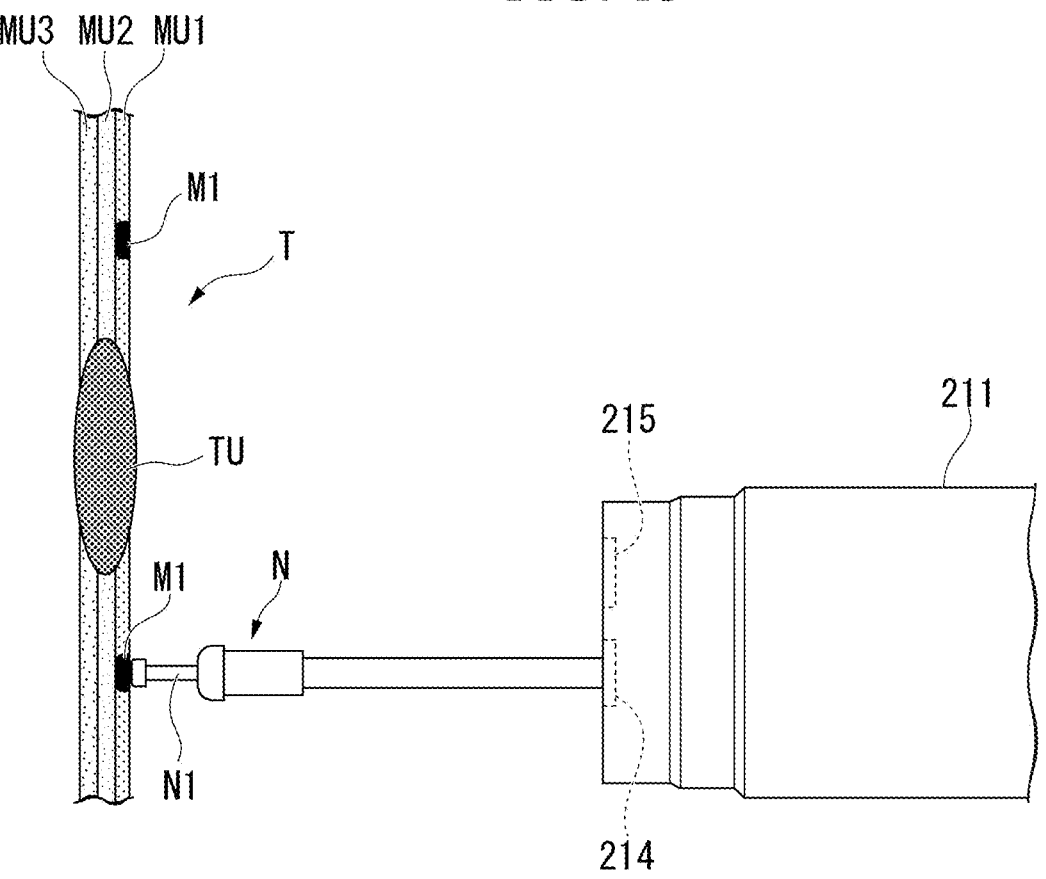
FIG. 13 is a view showing a marking step of the full-thickness resection method.

FIG. 13 is a view showing the marking step.

The surgeon inserts a high-frequency knife N as the marking treatment device into the treatment device channel 230 and protrudes the knife Ni provided at the distal end of the high-frequency knife N from the forceps port 214. The marking treatment device may be a high-frequency forceps, a high-frequency snare, a heating element such as a heat probe, an ultrasonic device, or the like.

Figure 14:
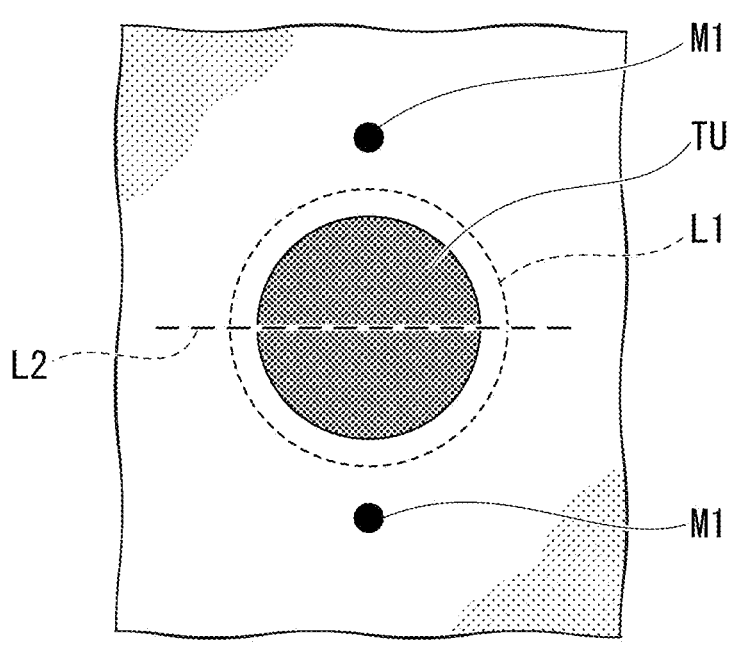
FIG. 14 is a view showing the generated marking.

FIG. 14 is a view showing the formed markings.

As shown in FIG. 14, the surgeon applies a pair of first markings M1 by pressing the knife Ni of the high-frequency knife N against the peripheral tissue surrounding the lesion TU in the treatment target T to cauterize the peripheral tissue. The pair of first markings M1 are formed in the peripheral tissue on both sides of the lesion TU. Specifically, the pair of first markings M1 are at the outside of the incision line L1 and formed in the peripheral tissue sandwiching the suture line L2 from both sides. It is desirable that the pair of first markings M1 are formed to sandwich the portion near the center of the lesion TU from both sides thereof.

As shown in FIG. 13, the marking M was applied by cauterizing the mucosal layer MU1, and the marking M does not reach the submucosal layer MU2 and the muscular layer MU3.

<Full-Thickness Resection Step>

Figure 15:
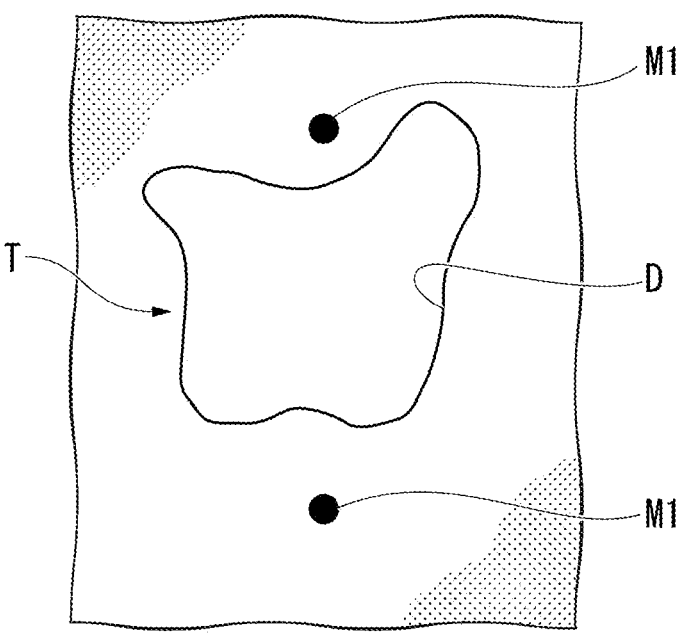
FIG. 15 is a view showing a treatment target to which the full-thickness resection is performed.
Figure 16:
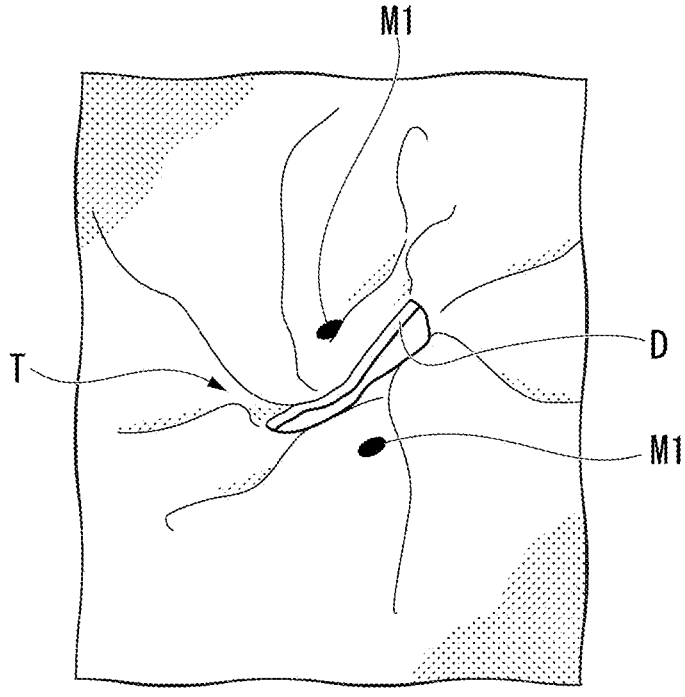
FIG. 16 is a view showing the treatment target to which the full-thickness resection is performed.

FIG. 15 and FIG. 16 are views showing the treatment target T being full-thickness resected.

The surgeon uses the high-frequency knife N to perform the full-thickness resection along the incision line L1. Since air in the stomach escapes to the abdominal cavity side from the defect D formed in the stomach by the full-thickness resection, the stomach collapses and deforms as shown in FIG. 16. Therefore, it becomes difficult to fit the entire defect D within the view field of the endoscope.

<Stapler Attachment Step>

After performing the line identification and circumferential incision, the surgeon removes the endoscope 200 and attaches the medical stapler 100 to the endoscope 200. The surgeon inserts again the insertion portion 210 of the endoscope 200 to which the medical stapler 100 is attached, and causes the distal end portion 211 to approach the treatment target T.

When the grasping portion 2 is in the open state, as shown in FIG. 9, the optical axis A1 of the objective lens 215 passes through the view field space 25 such that the surgeon can observe the treatment target T via the imaging unit of the endoscope 200.

<Grasping Step>

In the grasping step, the surgeon specifies the vicinity of the pair of first markings M1 as "a pair of first suture locations C1" and grasps the vicinity of the pair of first markings M1.

Figure 17:
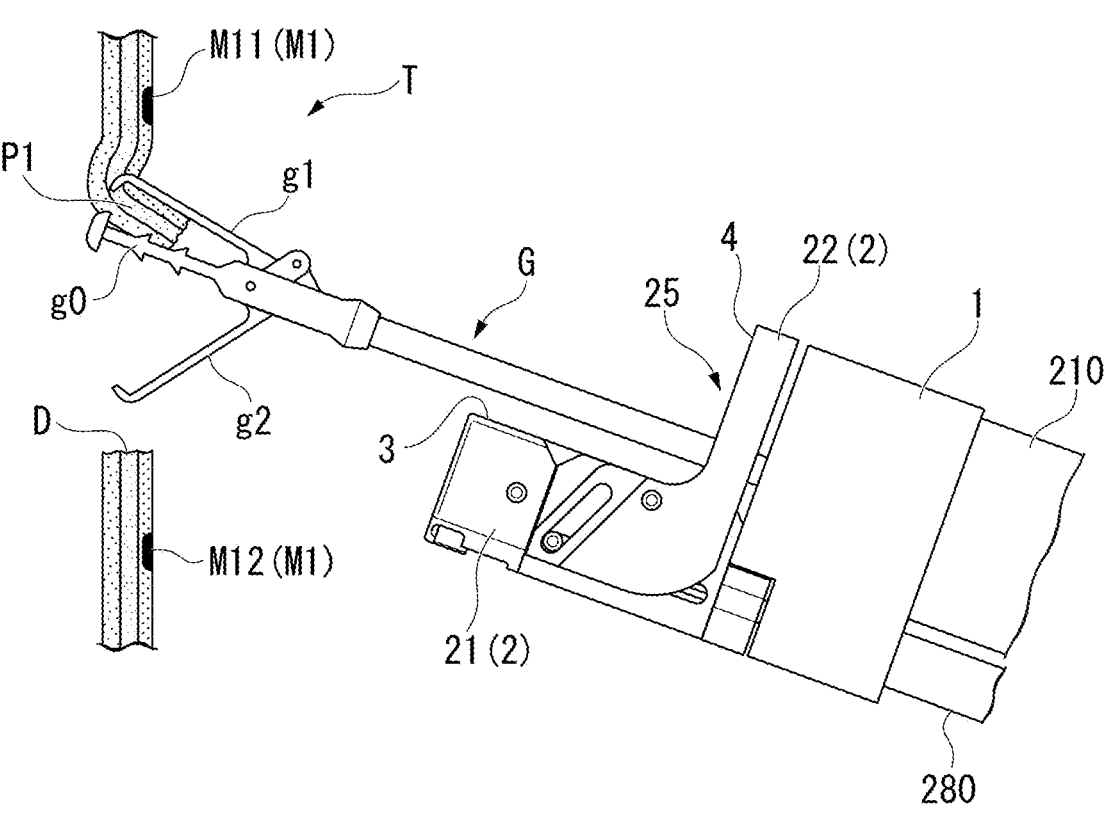
FIG. 17 is a view showing a grasping step of the full-thickness resection method.
Figure 18:
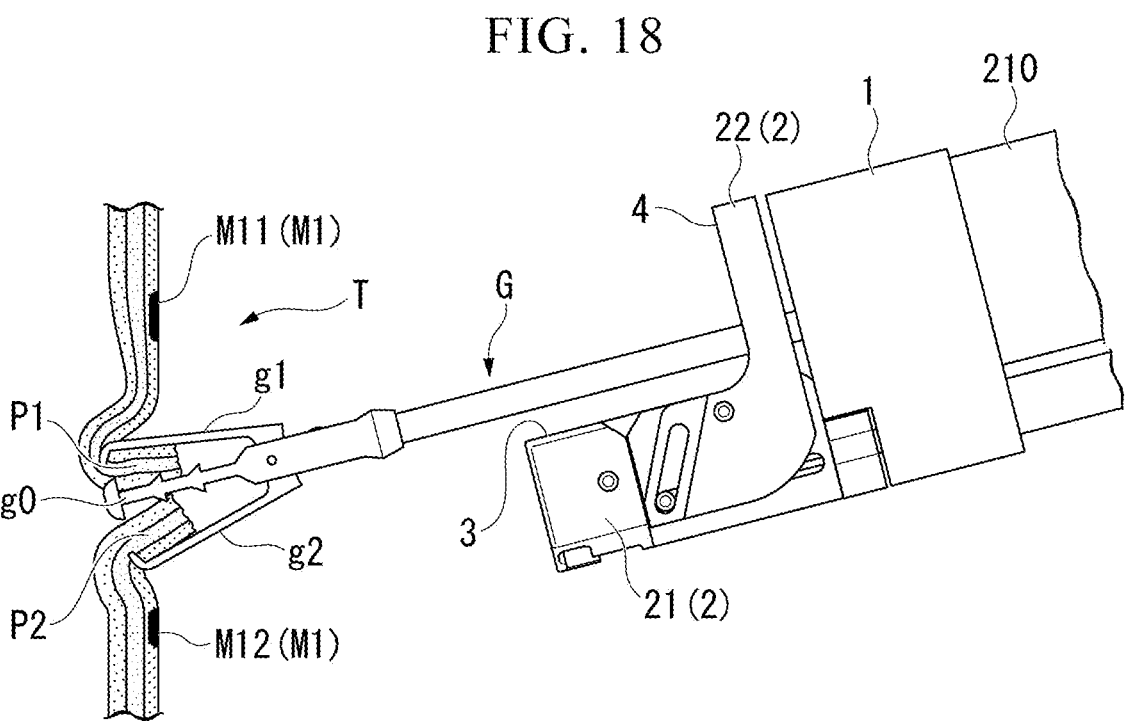
FIG. 18 is a view showing the grasping step of the full-thickness resection method.

FIG. 17 and FIG. 18 are views showing the grasping step.

The surgeon inserts a grasping forceps G as a retraction treatment device into the treatment device channel 230. The grasping forceps G includes a fixed forceps piece g0, a first forceps piece g1, and a second forceps piece g2. The first forceps piece g1 and the second forceps piece g2 are provided to be independently rotatable on both sides of the fixed forceps piece g0.

As shown in FIG. 17, the surgeon arranges the fixed forceps piece g0 in the vicinity of one side (M11) of the pair of first markings M1 on the edge of the defect D. Next, the surgeon closes the first grasping piece g1 arranged outside the fixed forceps piece g0, and pinches and grasps a first portion P1 of the surrounding tissue by the first grasping piece g1 and the fixed forceps piece g0 (first grasping step). The first portion P1 is a portion of the surrounding tissue located between the edge of the defect D and the one side (M11) of the pair of first markings M1.

As shown in FIG. 18, the surgeon places the fixed forceps piece g0 in the vicinity of the other side (M12) of the pair of first markings M1 on the edge of the defect D. The first portion P1 sandwiched between the first grasping piece g1 and the fixed forceps piece g0 is drawn to the vicinity of the other side (M12) of the pair of first markings M1. Next, the surgeon closes the second grasping piece g2 arranged outside the fixed forceps piece g1, and pinches and grasps the second portion P2 of the surrounding tissue with the second grasping piece g2 and the fixed forceps piece g0 (second grasping step). The second portion P2 is a portion of the surrounding tissue located between the edge of the defect D and the other side (M12) of the pair of first markings M1.

<Retraction Step>

Figure 19:
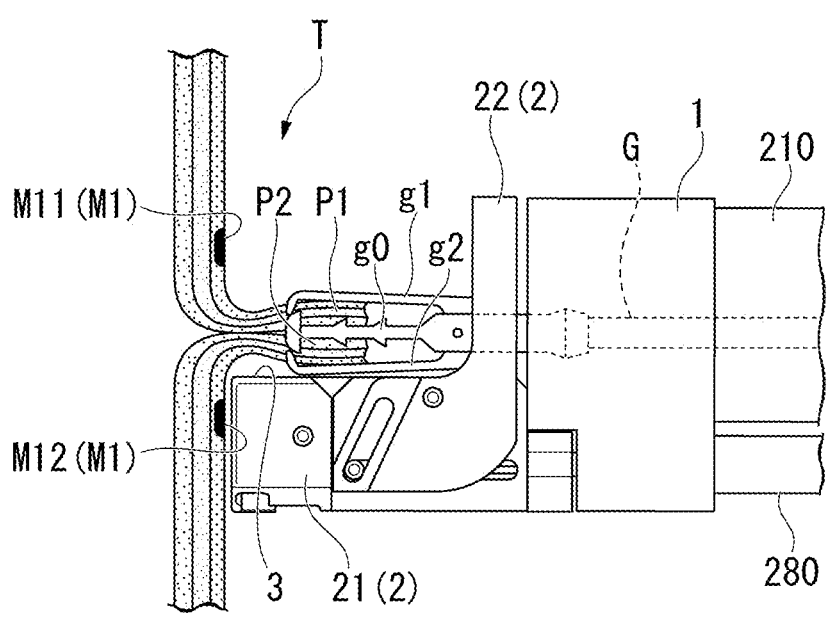
FIG. 19 is a view showing a retraction step of the full-thickness resection method.

FIG. 19 is a view showing the retraction step.

The surgeon pulls the first grasping piece g1 and the second grasping piece g2 together. The surgeon pulls the grasping forceps G toward the proximal-end side while grasping the first portion P1 and the second portion P2 of the surrounding tissue with the first grasping piece g1 and the second grasping piece g2. The surgeon retracts the grasping forceps G such that the distal end of the grasping forceps G is positioned at the proximal-end side with respect to the staple ejection portion 3.

<First Suturing Step>

Figure 20:
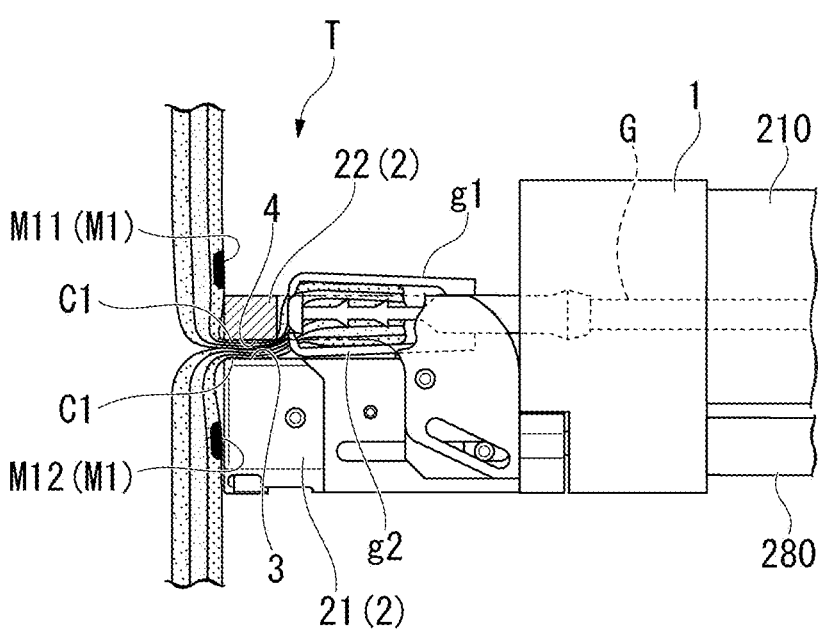
FIG. 20 is a view showing a suture step of the full-thickness resection method.
Figure 21:
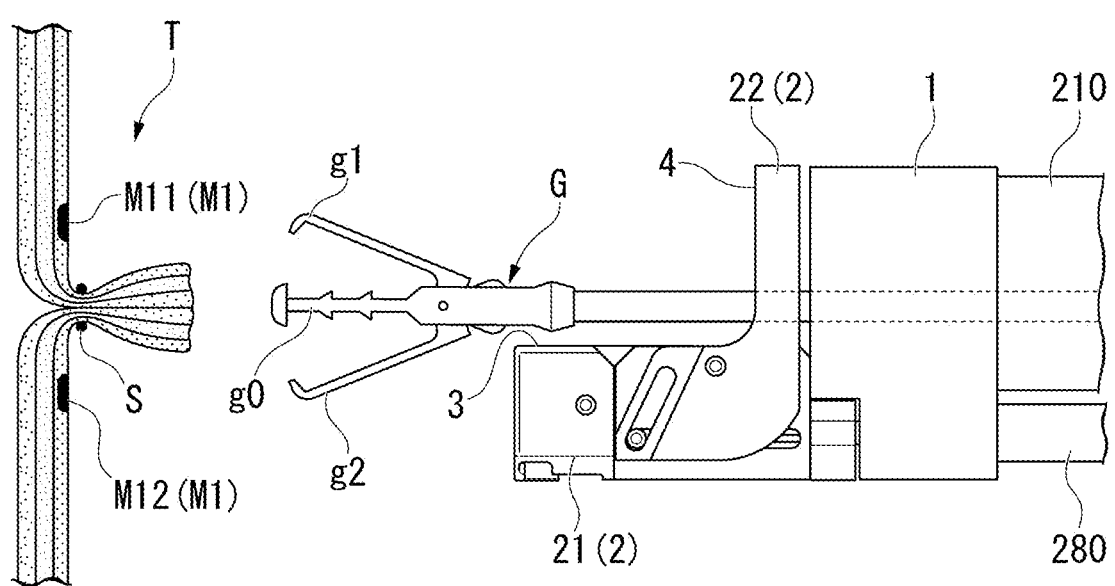
FIG. 21 is a view showing the suture step of the full-thickness resection method.

FIG. 20 and FIG. 21 are views showing the suturing steps.

The surgeon operates the open-close operation portion 250 to retract the open-close operation wire 5, thereby making the grasping portion 2 into the closed state. The surgeon clamps the pair of first suture locations C1 with the staple extraction portion 3 of the first grasping member 21 and the staple receiving portion 4 of the second grasping member 22, wherein the pair of first suture locations C1 are in the vicinity of the pair of first markings M1 positioned more outside of the defect D in the surrounding tissue than the first position P1 and the second portion P2.

When the grasping portion 2 is in the closed state, the optical axis A1 of the objective lens 215 passes through the upper side B1 of the first grasping member 21 and the second grasping member 22, as shown in FIG. 8. Therefore, the surgeon can observe the treatment target T through the imaging unit of the endoscope 200 even when the grasping portion 2 is in the closed state.

The surgeon operates the ejection operation portion 270 to pull the ejection operation wire 6 in the state in which the pair of first suture locations C1 are clamped between the staple ejection portion 3 and the staple receiving portion 4 so as to eject the stored staple S toward the staple receiving portion 4. The needle tip S1 of the staple S penetrates through the pair of first suture locations C1 and is bent by contacting the pocket 41 of the staple receiving portion 4. As a result, the pair of first suture locations C1 are sutured.

As shown in FIG. 21, the surgeon operates the open-close operation portion 250 to open the grasping portion 2 again. The surgeon opens the grasping forceps G and separates the grasping forceps G from the treatment target T.

Figure 22:
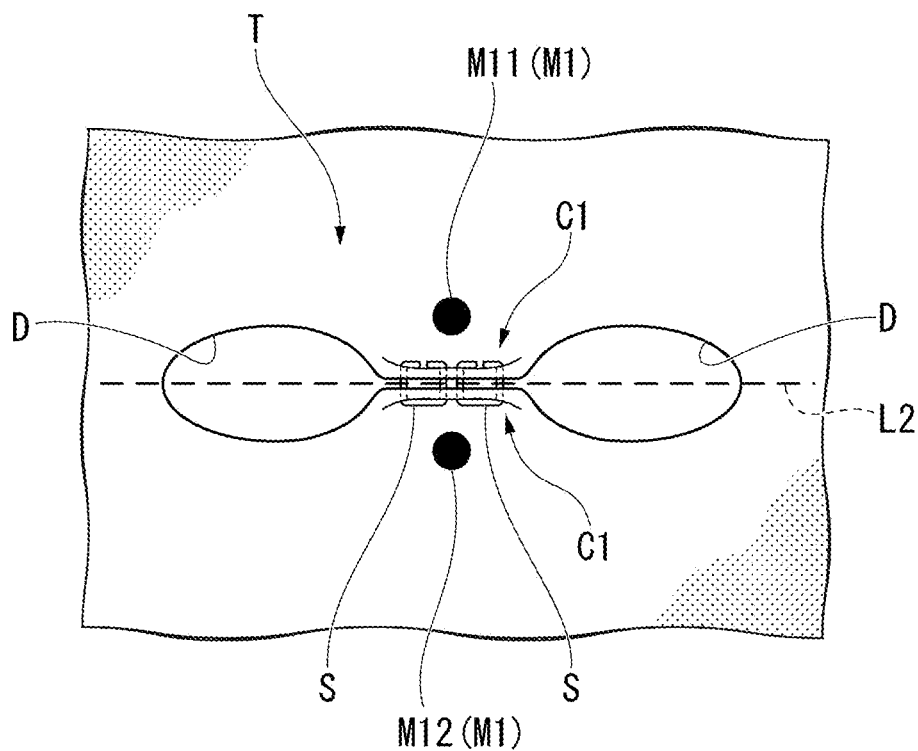
FIG. 22 is a view showing the treatment target where a pair of first suture locations are sutured.

FIG. 22 is a view showing the treatment target T to which a pair of first suture locations C1 are sutured.

The pair of first suture locations C1 are sutured along the suture line L2 with two staples S, as shown in FIG. 22.

<Second Suturing Step>

Figure 23:
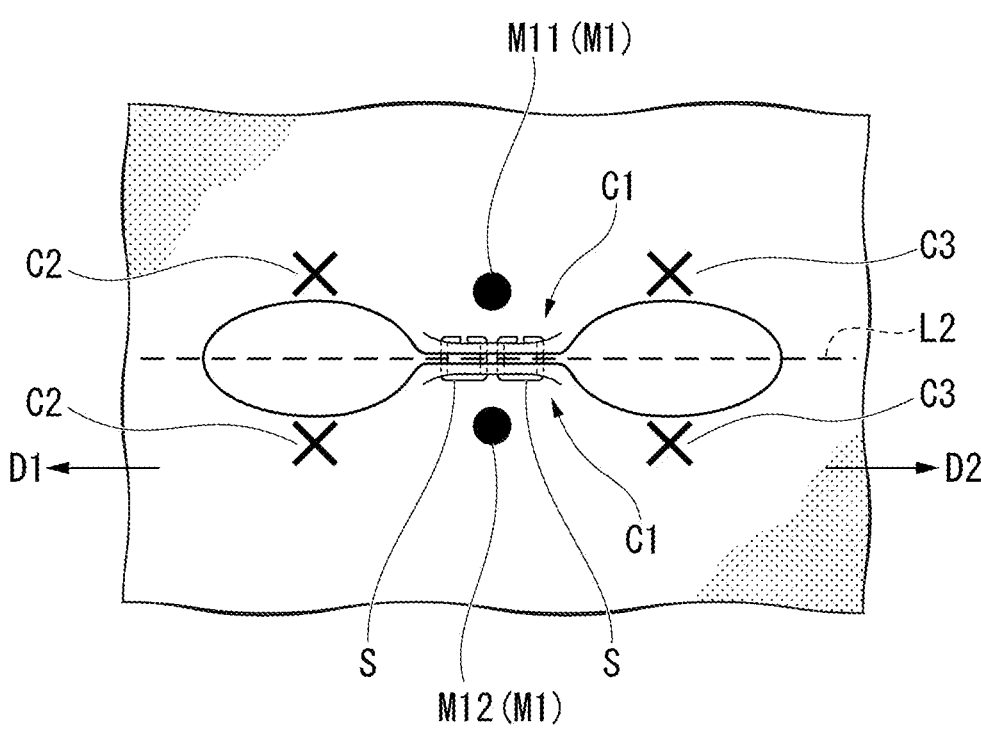
FIG. 23 is a view showing a pair of second suture locations and a pair of third suture locations.

FIG. 23 is a view showing a pair of second suture locations C2 and a pair of third suture locations C3.

The surgeon sutures the pair of second suture locations C2 positioned on one side (left side) D1 in the direction (left-right direction) along the suture line L2 with respect to the pair of first suture locations C1. The pair of second suture locations C2 are portions of the surrounding tissue located on both sides of the suture line L2 to sandwich the suture line L2. The suturing method is the same as that of the first suturing step.

<Third Suturing Step>

The surgeon sutures a pair of third suture locations C3 positioned on the other side (right side) D2 in the direction (left-right direction) along the suture line L2 with respect to the pair of first suture locations C1. The pair of third suture locations C3 are portions of the surrounding tissue located on both sides of the suture line L2 to sandwich the suture line L2. The suturing method is the same as that of the first suturing step.

It is desirable that a distance from the pair of first suture locations C1 to the pair of third suture locations C3 is substantially equal to a distance from the pair of first suture locations C1 to the pair of second suture locations C2. This is because it is easy to evenly arrange the suture locations in the left-right direction around the pair of first suture locations C1 as the center.

<Additional Suturing Step>

If the suturing of the defect D is insufficient, the surgeon performs suturing in other portions. When the suturing step is repeated and most of the peripheral portion of the defect D approaches, the surgeon inflates the stomach by sending air into the stomach and confirms the suturing state.

According to the method of full-thickness resection according to the present embodiment, when a full-thickness resection of a gastrointestinal tract such as the stomach is performed, even if the air in the gastrointestinal tract escapes to the abdominal cavity side and the gastrointestinal tract collapses and deforms, the surgeon can specify the pair of first suturing locations C1 to be sutured at first, and easily grasp the locations that should be sutured.

As described above, the first embodiment of the present disclosure has been described in detail with reference to the drawings; however, the specific configuration is not limited to this embodiment, and design changes and the like within the scope of the present disclosure are included. Also, the configurational elements shown in the above-described embodiment and modifications can be combined as appropriate.

Modification Example 1-1

In the above-described embodiment, the pair of first markings M1 are the markings formed by cauterizing the living tissue; however, the aspect of the pair of first markings is not limited to this configuration. The pair of first markings may be applied by a clip.

Second Embodiment

A second embodiment of the present disclosure will be described with reference to FIG. 24 to FIG. 25. In the following description, the same reference signs are given to the same configurations as those already described, and redundant descriptions will be omitted. The suturing method according to the second embodiment uses, for example, the medical system 300 shown in the first embodiment.

[Usage Method of the Medical Stapler 100]

A method of using the medical stapler 100 (a method of full-thickness resection using the medical stapler 100) will be explained.

<Insertion Step and Line Identification Step>

The surgeon performs the insertion step and the line identification step similar to the first embodiment.

<Marking Step>

Figure 24:
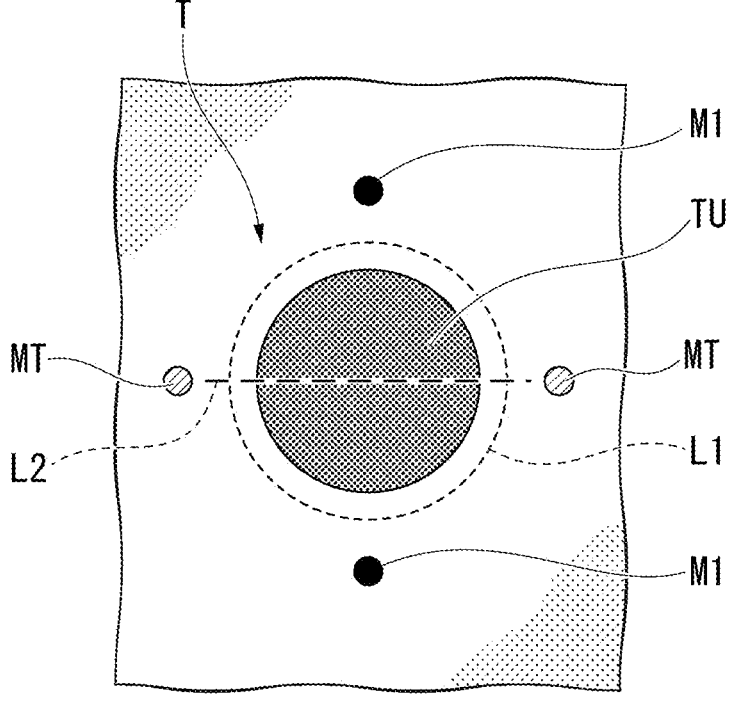
FIG. 24 is a view showing a marking step of a full-thickness resection method according to a second embodiment of the present disclosure.

FIG. 24 is a view showing the marking step.

Similar to the first embodiment, the surgeon applies the pair of first markings M1 to the surrounding tissues on both sides of the lesion TU. Furthermore, the surgeon applies a pair of end markings MT on the surrounding tissues on both sides of the lesion TU. The pair of end markings MT differs in shape and color from the pair of first markings M1. Therefore, the surgeon can visually distinguish between the pair of first markings M1 and the end markings MT.

The pair of first markings M1 are outside the incision line L1 and formed on the surrounding tissue on both sides of the suture line L2. The pair of end markings MT are formed in peripheral tissue on one side (left side) D1 and the other side (right side) D2 in the direction (left-right direction) along the suture line L2.

The pair of first markings M1 and the pair of end markings MT are preferably formed on both sides to sandwich the vicinity of the center of the lesion TU. In this case, the first straight line passing through the pair of first markings M1 intersects substantially perpendicularly with the second straight line passing through the pair of end markings MT.

<Full-Thickness Resection Step>

The surgeon performs the full-thickness resection along the incision line L1 with the high-frequency knife N, similar to the first embodiment.

<Grasping Step>

In the grasping step, the surgeon identifies the vicinity of the pair of first markings M1 as "the pair of first suture locations C1" and grasps the vicinity of the pair of first markings M1. The surgeon grasps the first portion P1 and the second portion P2 of the surrounding tissue with the grasping forceps G similar to the first embodiment.

<Retraction Step>

Similar to the first embodiment, the surgeon pulls the grasping forceps G toward the proximal-end side while grasping the first portion P1 and the second portion P2 of the surrounding tissue.

<First Suturing Step>

Figure 25:
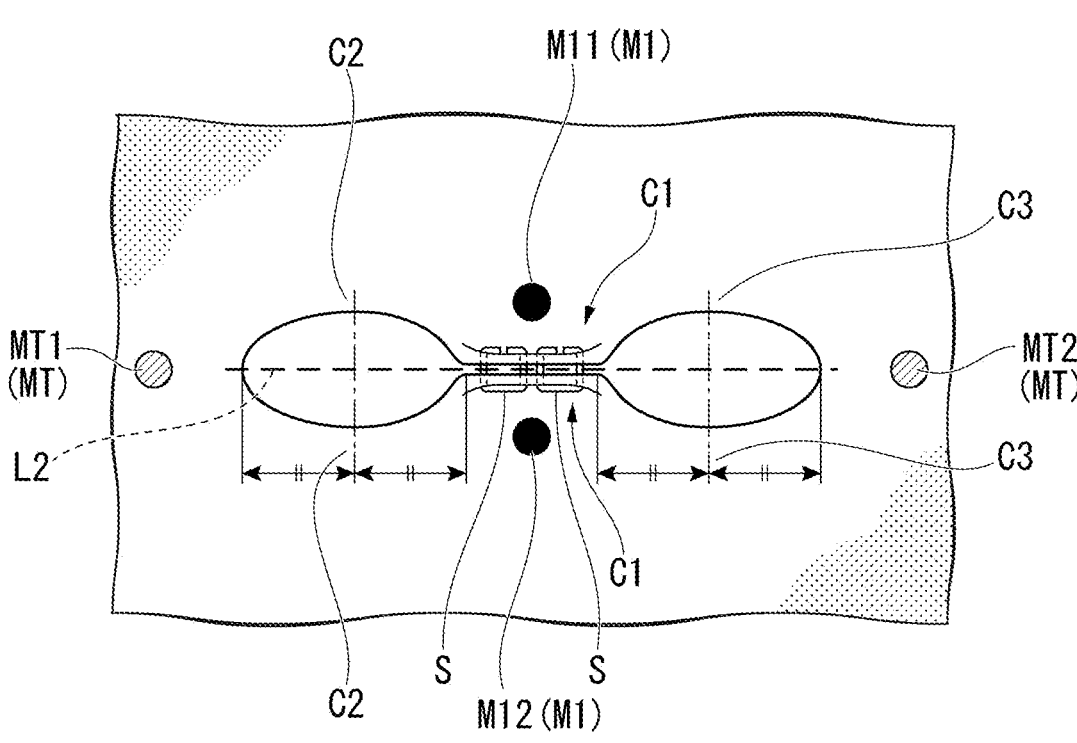
FIG. 25 is a view showing a treatment target where a pair of first suture locations are sutured.

FIG. 25 is a view showing the treatment target T to which the pair of first suture locations C1 are sutured.

The surgeon sutures the pair of first suture locations C1, similar to the first embodiment. The pair of first suture locations C1 are sutured along the suture line L2 with two staples S, as shown in FIG. 25.

<Second Suturing Step>

The surgeon sutures the pair of second suture locations C2 located between the pair of first suture locations C1 and one side (MT1) of the pair of end markings MT. The pair of second suture locations C2 are portions of the surrounding tissue located on both sides of the suture line L2. The pair of second seam points C2 is desirably positioned substantially at the center between the pair of first seam points C1 and one side (MT1) of the pair of end markings MT. The suturing method is the same as that in the first suturing step.

<Third Suturing Step>

The surgeon sutures the pair of third suture locations C3 located between the pair of first suture locations C1 and the other side (MT2) of the pair of end markings MT. The pair of third suture locations C3 are portions of the surrounding tissue located on both sides of the suture line L2. The pair of third suture locations C3 is desirably positioned substantially at the center between the pair of first seam points C1 and the other side (MT2) of the pair of end markings MT. The suturing method is the same as that in the first suturing step.

<Additional Suturing Step>

If the suturing of the defect D is insufficient, the surgeon sutures other portions. When the suturing step is repeated and most of the peripheral portion of the defect D approaches, the surgeon inflates the stomach by sending air into the stomach and confirms the suture state.

According to the method of full-thickness resection according to the present embodiment, when the full-thickness resection of a gastrointestinal tract such as the stomach is performed, even if the air in the gastrointestinal tract escapes to the abdominal cavity side and the gastrointestinal tract collapses and deforms, the surgeon can identify the pair of first suturing locations C1 to be sutured first, and easily grasp the places that should be sutured. Due to the pair of end markings MT, it is easy to specify the positions of the pair of second suture locations C2 and the pair of third suture locations C3 so as to effectively close the defect D.

As described above, the second embodiment of the present disclosure has been described in detail with reference to the drawings; however, the specific configuration is not limited to this embodiment, and design changes and the like within the scope of the present disclosure are included. Also, the configurational elements shown in the above-described embodiment and modifications can be combined as appropriate.

Modification Example 2-1

Figure 26:
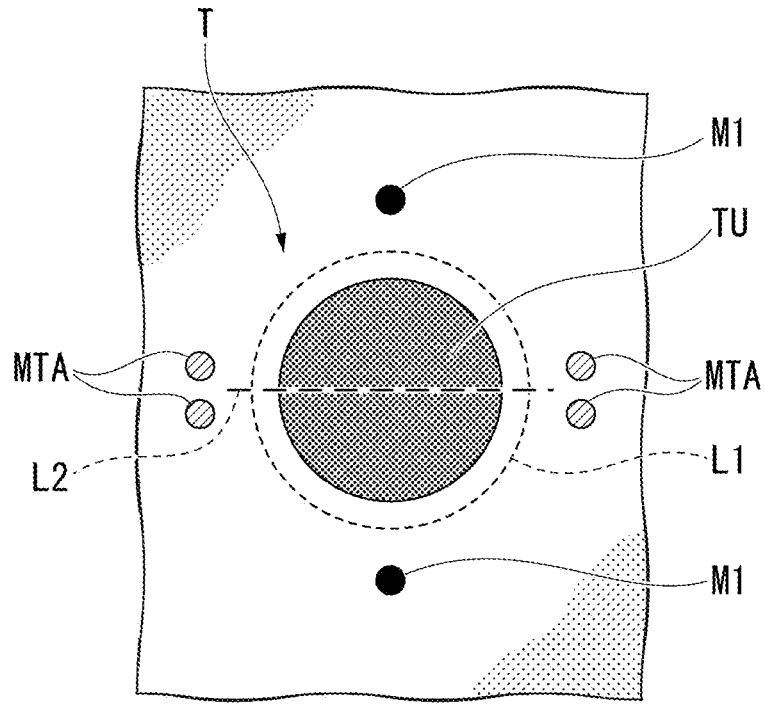
FIG. 26 is a view showing a modification example of the pair of second markings.

In the above-described embodiment, the pair of end markings MT differs in shape and color from the pair of first markings M1. However, the aspect of the pair of end markings that can be distinguished from the pair of first markings is not limited to this aspect. FIG. 26 shows a pair of end markings MTA, which is a modification example of the pair of end markings MT. The pair of end markings MTA are markings provided at two locations on each of one side (left side) D1 and the other side (right side) D2 in the direction (left-right direction) along the suture line L2. The pair of end markings MTA is easier to visually distinguish from the pair of end markings MT.

Modification Example 2-2

Figure 27:
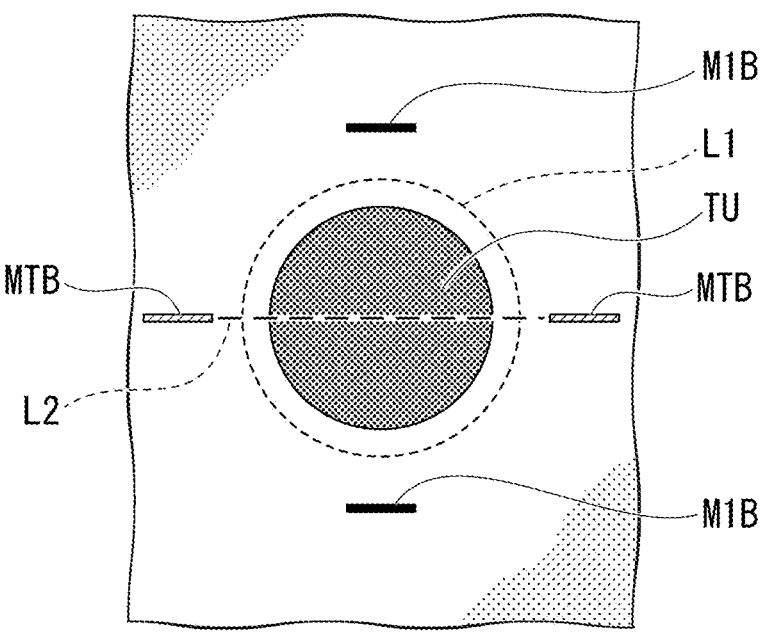
FIG. 27 is a view showing the modification examples of the pair of second markings M1 and the pair of second markings M2.

FIG. 27 is a view showing a pair of first markings M1B, which is a modification of the pair of second markings M1, and a pair of end markings MTB, which is a modification of the pair of end markings MT. The pair of first markings M1B are line segments substantially parallel to the suture line L2. The pair of end markings MTB are line segments substantially parallel to the suture line L2. The surgeon may visually distinguish the pair of first markings M1B from the pair of end markings MTB from the direction of the line segment with respect to the lesion TU (defect D).

Third Embodiment

A third embodiment of the present disclosure will be described with reference to FIG. 28 to FIG. 29. In the following description, the same reference signs are given to the same configurations as those already described, and redundant descriptions will be omitted. The suturing method according to the third embodiment uses, for example, the medical system 300 shown in the first embodiment.

[Usage Method of the Medical Stapler 100]

A method of using the medical stapler 100 (a method of full-thickness resection using the medical stapler 100) will be explained.

<Insertion Step and Line Identification Step>

The surgeon performs the insertion step and the line certification step as in the first embodiment.

<Marking Step>

Figure 28:
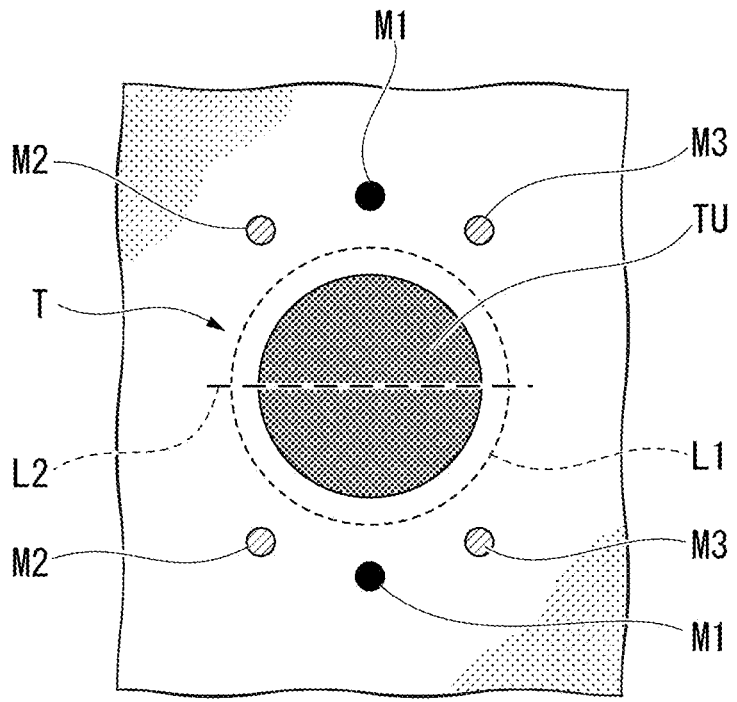
FIG. 28 is a view showing a view of a marking step in a full-thickness resection method according to a third embodiment of the present disclosure.

FIG. 28 is a view showing the marking step.

Similar to the first embodiment, the surgeon applies the pair of first markings M1 to the surrounding tissues on both sides of the lesion TU. Furthermore, the surgeon applies a pair of second markings M2 and a pair of second markings M3 on the surrounding tissues on both sides of the lesion TU. The pair of second markings M2 and the pair of second markings M3 are different in shape and color from the pair of first markings M1. Therefore, the surgeon can visually distinguish the pair of first markings M1 from the pair of second markings M2 and the pair of second markings M3. The pair of first markings M1, the pair of second markings M2, and the pair of second markings M3 may be different in shape and color so as to be visually distinguishable from each other.

The pair of first markings M1 are outside the incision line L1 and formed on the surrounding tissue on both sides to sandwich the suture line L2. The pair of second markings M2 are formed in the surrounding tissues on both sides to sandwich the suture line L2, and are formed in the surrounding tissue on one side (left side) D1 in the direction (left-right direction) along the suture line L2 with respect to the pair of first markings M1. The pair of second markings M3 are formed in the surrounding tissue on both sides to sandwich the suture line L2, and are formed in the surrounding tissue on the other side (right side) D2 in the direction (left-right direction) along the suture line L2 with respect to the pair of first markings M1.

<Full-Thickness Resection Step>

The surgeon performs the full-thickness resection along the incision line L1 with the high-frequency knife N, similar to the first embodiment.

<Grasping Step>

The Surgeon Identifies the Vicinity of the Pair of first markings M1 as "the pair of first suture locations C1" and grasps the vicinity of the pair of first markings M1. The surgeon grasps the first portion P1 and the second portion P2 of the surrounding tissue with the grasping forceps G similar to the first embodiment.

<Retraction Step>

Similar to the first embodiment, the surgeon pulls the grasping forceps G toward the proximal-end side while grasping the first portion P1 and the second portion P2 of the surrounding tissue.

<First Suturing Step>

Figure 29:
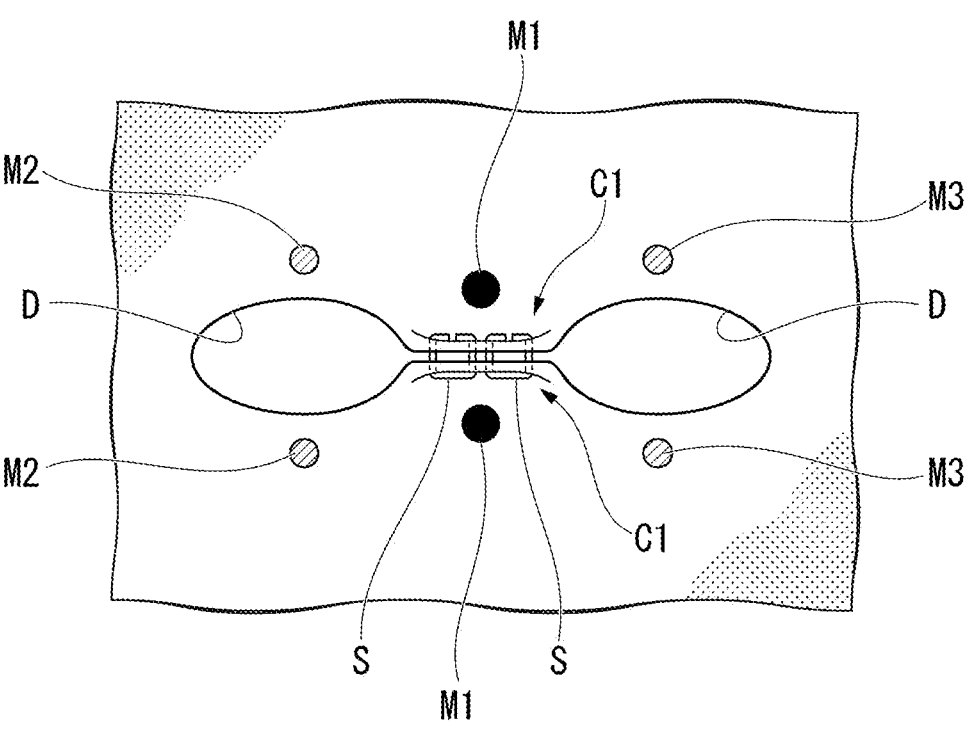
FIG. 29 is a view showing the treatment target where the pair of first suture locations are sutured.

FIG. 29 is a view showing a treatment target T to which the pair of first suture locations C1 are sutured.

The surgeon sutures the pair of first suture locations C1, similar to the first embodiment. The pair of first suture locations C1 are sutured along the suture line L2 with two staples S, as shown in FIG. 29.

<Second Suturing Step>

The surgeon identifies the vicinity of the pair of second markings M2 as the "pair of second suture locations C2" and sutures the pair of second suture locations C2. The suturing method is the same as that in the first suturing step.

<Third Suture Step>

The surgeon identifies the vicinity of the pair of third markings M2 as "the pair of third suture locations C2" and sutures the pair of second suture locations C2. The suturing method is the same as that in the first suturing step.

<Additional Suture Step>

If the suturing of the defect D is insufficient, the surgeon sutures other portions. When the suturing step is repeated and most of the peripheral portion of the defect D approaches, the surgeon inflates the stomach by sending air into the stomach and confirms the suture state.

According to the method of full-thickness resection according to the present embodiment, when a full-thickness resection of the gastrointestinal tract such as the stomach is performed, even if the air in the gastrointestinal tract escapes to the abdominal cavity side and the gastrointestinal tract collapses and deforms, the surgeon can specify the pair of first suturing points C1 to be sutured first, and easily grasp the places that should be sutured. Due to the pair of second markings M2 and the pair of third markings M3, it is easy to specify the positions of the pair of second suture locations C and the pair of third suture locations C3.

As described above, the third embodiment of the present disclosure has been described in detail with reference to the drawings; however, the specific configuration is not limited to this embodiment, and design changes and the like are included within the scope of the present disclosure. Also, the constituent elements shown in the above-described embodiment and modifications can be combined as appropriate.

Modification Example 3

In the above embodiment, the medical stapler 100 is used for suturing; however, the suturing method is not limited to this aspect. The suturing operation may be with a suture needle and suture thread.

What is claimed is:

1. A full-thickness resection method for a gastrointestinal tract, wherein a stomach of the gastrointestinal tract is resected, the method comprising, in the following order:

forming a pair of first markings in surrounding tissue on both sides of a lesion to sandwich the lesion therebetween;

performing a full-thickness resection to a portion of the surrounding tissue along an incision line surrounding the lesion;

identifying a pair of first suture locations in the vicinity of the pair of first markings;

pulling together edges of a hole created by the full-thickness resection while suturing the pair of first suture locations, wherein the edges are captured and pulled together by grasping forceps that include a fixed forceps piece, a first forceps piece, and a second forceps piece, and the first forceps piece and the second forceps piece are independently rotatable on both sides of the fixed forceps piece; and inflating the stomach with air.

2. The full-thickness resection method according to claim 1, wherein the pair of first markings are formed in the surrounding tissues on both sides of the lesion to sandwich a portion in the vicinity of a center of the lesion.

3. The full-thickness resection method according to claim 1, further comprising identifying a suture line for suturing a defect portion due to the full-thickness resection, wherein the pair of first markings are formed in the surrounding tissue on both sides to sandwich the suture line.

4. The full-thickness resection method according to claim 3, further comprising:

after the pair of first suture locations are sutured, suturing a pair of second suture locations positioned on one side with respect to the pair of first suture locations in a direction along the suture line; and suturing a pair of third suture locations positioned on the other side with respect to the pair of first suture locations in the direction along the suture line.

5. The full-thickness resection method according to claim 4, wherein a distance from the pair of first suture locations to the pair of third suture locations is substantially the same with a distance from the pair of first suture locations to the pair of second suture locations.

6. A full-thickness resection method for a gastrointestinal tract, comprising, in the following order:

forming a pair of first markings in surrounding tissue on both sides of a lesion to sandwich the lesion therebetween, wherein the pair of first markings are formed at two points along a line perpendicular to a suture line;

forming a pair of end markings in the surrounding tissue on both sides of the lesion to sandwich the lesion therebetween, wherein the pair of end markings are formed at two points on either side of the suture line;

performing a full-thickness resection to a portion of the surrounding tissue along an incision line surrounding the lesion;

identifying a pair of first suture locations in the vicinity of the pair of first markings;

pulling together edges of a bole created by the full-thickness resection while suturing the pair of first suture locations;

pulling together the edges of the hole while suturing a pair of second suture locations positioned between the pair of first suture locations and one side of the pair of end markings; and pulling together the edges of the hole while suturing a pair of third suture locations positioned between the pair of first suture locations and the other side of the pair of end markings, wherein the edges of the hole are captured and pulled together by grasping forceps that include a fixed forceps piece, a first forceps piece, and a second forceps piece, and the first forceps piece and the second forceps piece are independently rotatable on both sides of the fixed forceps piece.

7. The full-thickness resection method according to claim 6, wherein the pair of first markings are different in shape from the pair of end markings.

8. The full-thickness resection method according to claim 6, further comprising:

identifying the suture line for suturing a defect portion due to the full-thickness resection, wherein the pair of first markings are formed in the surrounding tissue on both sides to sandwich the suture line, and the pair of end markings are formed in the surrounding tissue on one side and the other side of a direction along the suture line.

9. The full-thickness resection method according to claim 6, wherein the pair of first markings are formed in the surrounding tissue on both sides to sandwich a center of the lesion, the pair of end markings are formed in the surrounding tissue on both sides to sandwich the center of the lesion, and a first straight line passing through the pair of first markings intersects substantially perpendicularly with a second straight line passing through the pair of end markings.

10. A full-thickness resection method for a gastrointestinal tract, comprising, in the following order:

identifying a suture line for suturing a defect portion due to the full-thickness resection;

forming a pair of first markings in surrounding tissue on both sides of a lesion to sandwich the lesion therebetween, wherein the pair of first markings are formed at two points along a first line perpendicular to the suture line;

forming a pair of second markings in the surrounding tissue on both sides to sandwich the suture line, wherein the pair of second markings are formed at two points along a second line perpendicular to the suture line;

forming a pair of third markings in the surrounding tissue on both sides to sandwich the suture line, wherein the pair of third markings are formed at two points along a third line perpendicular to the suture line;

performing a full-thickness resection to a portion of the surrounding tissue along an incision line surrounding the lesion;

identifying a pair of first suture locations in the vicinity of the pair of first markings;

pulling together edges of a bole created by the full thickness resection while suturing the pair of first suture locations;

identifying a pair of second suture locations in the vicinity of the pair of second markings;

pulling together the edges of the hole while suturing the pair of second suture locations;

identifying a pair of third suture locations in the vicinity of the pair of third markings; and pulling together the edges of the hole while suturing the pair of third suture locations, wherein the edges of the hole are captured and pulled together by grasping forceps that include a fixed forceps piece, a first forceps piece, and a second forceps piece, and the first forceps piece and the second forceps piece are independently rotatable on both sides of the fixed forceps piece.

11. The full-thickness resection method according to claim 10, wherein the pair of second markings are formed in the surrounding tissue on one side of the suture line with respect to the pair of first markings, and the pair of third markings are formed in the surrounding tissue on the other side of the suture line with respect to the pair of first markings.

12. The full-thickness resection method according to claim 11, wherein a distance from the pair of first suture locations to the pair of third suture locations is substantially the same with a distance from the pair of first suture locations to the pair of second suture locations.

\*   \*   \*   \*   \*